(12) United States Patent
Chronos et al.

(10) Patent No.: US 11,615,257 B2
(45) Date of Patent: Mar. 28, 2023

(54) METHOD FOR COMMUNICATING WITH IMPLANT DEVICES

(71) Applicant: ENDOTRONIX, INC., Lisle, IL (US)

(72) Inventors: Nicholas Chronos, Lisle, IL (US); Michael L. Nagy, Lisle, IL (US); Douglas A. Nielsen, Lisle, IL (US); Balamurugan Sundaram, Lisle, IL (US); Suresh Sundaram, Lisle, IL (US)

(73) Assignee: ENDOTRONIX, INC., Lisle, IL (US)

( * ) Notice: Subject to any disclaimer, the term of this patent is extended or adjusted under 35 U.S.C. 154(b) by 107 days.

(21) Appl. No.: 17/140,582

(22) Filed: Jan. 4, 2021

(65) Prior Publication Data

US 2021/0216733 A1 Jul. 15, 2021

Related U.S. Application Data

(63) Continuation-in-part of application No. 16/588,192, filed on Sep. 30, 2019, which is a continuation of
(Continued)

(51) Int. Cl.
*G06K 7/10* (2006.01)
*A61B 90/98* (2016.01)
(Continued)

(52) U.S. Cl.
CPC ........ *G06K 7/10425* (2013.01); *A61B 5/0031* (2013.01); *A61B 5/0215* (2013.01);
(Continued)

(58) Field of Classification Search
None
See application file for complete search history.

(56) References Cited

U.S. PATENT DOCUMENTS

| 3,714,595 A | 1/1973 | Denenberg |
| 3,872,455 A | 3/1975 | Fuller |

(Continued)

FOREIGN PATENT DOCUMENTS

| EP | 2612595 | 7/2013 |
| HK | 1147906 | 8/2011 |

(Continued)

OTHER PUBLICATIONS

The International bureau of WIPO, International Search Report and Written Opinion of the International Searching Authority, dated Aug. 25, 2010, International App. No. PCT/US10/27951, Applicant Endotronix, Inc.

(Continued)

*Primary Examiner* — Santiago Garcia
(74) *Attorney, Agent, or Firm* — McDonald Hopkins LLC

(57) ABSTRACT

Disclosed is a reader device, system, and method for communicating with a wireless sensor. The reader device may be configured to communicate wirelessly with an implant device associated with a proprietary system provided by a first entity. An external device, that may not be associated with said first entity, is provided and is configured to be calibrated to communicate with the implant device that is located within a patient. The external device may be used in place of an existing reader device that was initially calibrated to communicate with the implant device prior to the implant device being placed within the patient. The external device may be particularly useful for implant devices that communicate wirelessly with external devices where said implant devices are intended to be located within the human body on a permanent or indefinite duration of time.

24 Claims, 9 Drawing Sheets

Related U.S. Application Data application No. 15/903,809, filed on Feb. 23, 2018, now Pat. No. 10,430,624.

(60) Provisional application No. 62/956,686, filed on Jan. 3, 2020, provisional application No. 62/463,203, filed on Feb. 24, 2017.

(51) Int. Cl.
*A61B 5/00* (2006.01)
*A61B 5/0215* (2006.01)
*H04Q 9/00* (2006.01)
*G16H 10/65* (2018.01)
*A61B 5/318* (2021.01)

(52) U.S. Cl.
CPC .......... *A61B 90/98* (2016.02); *G06K 7/10386* (2013.01); *H04Q 9/00* (2013.01); *A61B 5/318* (2021.01); *A61F 2250/0002* (2013.01); *B81B 2201/02* (2013.01); *B81B 2201/06* (2013.01); *G16H 10/65* (2018.01); *H04Q 2209/00* (2013.01); *H04Q 2209/47* (2013.01); *H04Q 2209/50* (2013.01); *H04Q 2209/86* (2013.01)

(56) References Cited

U.S. PATENT DOCUMENTS

| | | |
|---|---|---|
| 3,888,708 A | 6/1975 | Wise |
| 3,943,915 A | 3/1976 | Severson |
| 3,958,558 A | 5/1976 | Dunphy |
| 4,023,562 A | 5/1977 | Hynecek |
| 4,026,276 A | 5/1977 | Chubbuck |
| 4,037,324 A | 7/1977 | Andreasen |
| 4,067,235 A | 1/1978 | Markland |
| 4,127,110 A | 11/1978 | Bullara |
| 4,206,762 A | 6/1980 | Cosman |
| 4,385,636 A | 5/1983 | Cosman |
| 4,407,296 A | 10/1983 | Anderson |
| 4,485,813 A | 12/1984 | Anderson |
| 4,511,858 A | 4/1985 | Charavit |
| 4,531,244 A | 7/1985 | Hamas |
| 4,531,526 A | 7/1985 | Genest |
| 4,567,459 A | 1/1986 | Folger |
| 4,644,420 A | 2/1987 | Buchan |
| 4,651,089 A | 3/1987 | Haigh |
| 4,701,826 A | 10/1987 | Mikkor |
| 4,730,496 A | 3/1988 | Knecht |
| 4,815,472 A | 3/1989 | Wise |
| 4,881,410 A | 11/1989 | Wise |
| 4,953,387 A | 9/1990 | Johnson |
| 4,966,034 A | 10/1990 | Bock |
| 5,005,577 A | 4/1991 | Frenkel |
| 5,006,819 A | 4/1991 | Buchan |
| 5,013,396 A | 5/1991 | Wise |
| 5,046,497 A | 9/1991 | Millar |
| 5,055,838 A | 10/1991 | Wise |
| 5,059,543 A | 10/1991 | Wise |
| 5,108,420 A | 4/1992 | Marks |
| 5,113,868 A | 5/1992 | Wise |
| 5,227,798 A | 7/1993 | Hildebrand |
| 5,257,630 A | 11/1993 | Broitman |
| 5,262,127 A | 11/1993 | Wise |
| 5,282,827 A | 2/1994 | Kensey |
| 5,296,255 A | 3/1994 | Gland |
| 5,334,952 A | 8/1994 | Maddy |
| 5,343,064 A | 8/1994 | Spangler |
| 5,377,524 A | 1/1995 | Wise |
| 5,417,235 A | 5/1995 | Wise |
| 5,522,267 A | 6/1996 | Lewis |
| 5,564,434 A | 10/1996 | Halperin |
| 5,581,248 A | 12/1996 | Spillman |
| 5,690,674 A | 11/1997 | Diaz |
| 5,872,520 A | 2/1999 | Seifert |
| 5,920,233 A | 7/1999 | Denny |
| 5,992,769 A | 11/1999 | Wise |
| 6,015,386 A | 1/2000 | Kensey |
| 6,024,704 A | 2/2000 | Meador |
| 6,025,725 A | 2/2000 | Gershenfeld |
| 6,053,873 A | 4/2000 | Govari |
| 6,109,113 A | 8/2000 | Chavan |
| 6,111,520 A | 8/2000 | Allen |
| 6,126,675 A | 10/2000 | Shchervinsky |
| 6,140,144 A | 10/2000 | Najafi |
| 6,150,681 A | 11/2000 | Allen |
| 6,171,252 B1 | 1/2001 | Roberts |
| 6,174,322 B1 | 1/2001 | Schneidt |
| 6,190,400 B1 | 2/2001 | Van De Moer |
| 6,206,835 B1 | 3/2001 | Spillman |
| 6,232,150 B1 | 5/2001 | Lin |
| 6,278,379 B1 | 8/2001 | Allen |
| 6,287,256 B1 | 9/2001 | Park |
| 6,309,350 B1 | 10/2001 | VanTassel |
| 6,312,380 B1 | 11/2001 | Hoek |
| 6,331,163 B1 | 12/2001 | Kaplan |
| 6,338,284 B1 | 1/2002 | Najafi |
| 6,359,444 B1 | 3/2002 | Grimes |
| 6,378,360 B1 | 4/2002 | Bartels |
| 6,416,474 B1 | 7/2002 | Penner |
| 6,432,737 B1 | 8/2002 | Webster |
| 6,441,503 B1 | 8/2002 | Webster |
| 6,442,413 B1 | 8/2002 | Silver |
| 6,447,449 B1 | 9/2002 | Fleischman |
| 6,454,720 B1 | 9/2002 | Clerc |
| 6,459,253 B1 | 10/2002 | Krusell |
| 6,471,656 B1 | 10/2002 | Shalman |
| 6,477,901 B1 | 11/2002 | Tadigadapa |
| 6,499,354 B1 | 12/2002 | Najafi |
| 6,505,516 B1 | 1/2003 | Frick |
| 6,517,481 B2 | 2/2003 | Hoek |
| 6,532,834 B1 | 3/2003 | Pinto |
| 6,535,116 B1 | 3/2003 | Zhou |
| 6,570,457 B2 | 5/2003 | Fischer |
| 6,579,235 B1 | 6/2003 | Abita |
| 6,592,608 B2 | 7/2003 | Fisher |
| 6,636,769 B2 | 10/2003 | Govari |
| 6,645,143 B2 | 11/2003 | VanTassel |
| 6,647,778 B2 | 11/2003 | Sparks |
| 6,658,300 B2 | 12/2003 | Govari |
| 6,662,663 B2 | 12/2003 | Chen |
| 6,666,826 B2 | 12/2003 | Salo |
| 6,667,725 B1 | 12/2003 | Simons |
| 6,680,654 B2 | 1/2004 | Fischer |
| 6,682,490 B2 | 1/2004 | Roy |
| 6,713,828 B1 | 3/2004 | Chavan |
| 6,749,568 B2 | 6/2004 | Fleischman |
| 6,749,622 B2 | 6/2004 | McGuckin |
| 6,757,566 B2 | 6/2004 | Weiner |
| 6,764,446 B2 | 7/2004 | Wolinsky |
| 6,779,406 B1 | 8/2004 | Kuznia |
| 6,783,499 B2 | 8/2004 | Schwartz |
| 6,789,429 B2 | 9/2004 | Pinto |
| 6,805,667 B2 | 10/2004 | Christopherson |
| 6,824,521 B2 | 11/2004 | Rich |
| 6,838,640 B2 | 1/2005 | Wise |
| 6,840,956 B1 | 1/2005 | Wolinsky |
| 6,844,213 B2 | 1/2005 | Sparks |
| 6,855,115 B2 | 2/2005 | Fonseca |
| 6,890,300 B2 | 5/2005 | Lloyd |
| 6,893,885 B2 | 5/2005 | Lemmerhirt |
| 6,916,310 B2 | 7/2005 | Sommerich |
| 6,923,625 B2 | 8/2005 | Sparks |
| 6,926,670 B2 | 8/2005 | Rich |
| 6,932,114 B2 | 8/2005 | Sparks |
| 6,935,010 B2 | 8/2005 | Tadigadpa |
| 6,939,299 B1 | 9/2005 | Petersen |
| 6,945,939 B2 | 9/2005 | Turcott |
| 6,959,608 B2 | 11/2005 | Bly |
| 6,968,743 B2 | 11/2005 | Rich |
| 6,981,958 B1 | 1/2006 | Gharib |
| 6,994,666 B2 | 2/2006 | Shannon |
| 6,994,672 B2 | 2/2006 | Fleischman |
| 7,001,398 B2 | 2/2006 | Carley |
| 7,004,015 B2 | 2/2006 | Chang-Chien |

(56) References Cited

U.S. PATENT DOCUMENTS

| | | |
|---|---|---|
| 7,004,034 B2 | 2/2006 | Chen |
| 7,013,734 B2 | 3/2006 | Zdeblick |
| 7,018,337 B2 | 3/2006 | Hood |
| 7,025,727 B2 | 4/2006 | Brockway |
| 7,025,778 B2 | 4/2006 | Hayashi |
| 7,028,550 B2 | 4/2006 | Zdeblick |
| 7,046,964 B1 | 5/2006 | Sullivan |
| 7,048,756 B2 | 5/2006 | Eggers |
| 7,059,176 B2 | 6/2006 | Sparks |
| 7,059,195 B1 | 6/2006 | Liu |
| 7,059,196 B1 | 6/2006 | Liu |
| 7,065,459 B2 | 6/2006 | Kalinin |
| 7,066,031 B2 | 6/2006 | Zdeblick |
| 7,073,387 B2 | 7/2006 | Zdeblick |
| 7,081,125 B2 | 7/2006 | Edwards |
| 7,131,945 B2 | 11/2006 | Fink |
| 7,134,341 B2 | 11/2006 | Girmonsky |
| 7,137,953 B2 | 11/2006 | Eigler |
| 7,146,861 B1 | 12/2006 | Cook |
| 7,147,604 B1 | 12/2006 | Allen |
| 7,149,587 B2 | 12/2006 | Wardle |
| 7,162,926 B1 | 1/2007 | Guziak |
| 7,169,106 B2 | 1/2007 | Fleischman |
| 7,181,975 B1 | 2/2007 | Bradley |
| 7,190,937 B1 | 3/2007 | Sullivan |
| 7,191,013 B1 | 3/2007 | Miranda et al. |
| 7,192,001 B2 | 3/2007 | Wise |
| 7,198,603 B2 | 4/2007 | Penner |
| 7,211,048 B1 | 5/2007 | Najafi |
| 7,219,021 B2 | 5/2007 | Liu |
| 7,228,735 B2 | 6/2007 | Sparks |
| 7,245,117 B1 | 7/2007 | Joy |
| 7,252,006 B2 | 8/2007 | Tai |
| 7,252,010 B2 | 8/2007 | Ohta |
| 7,254,244 B2 | 8/2007 | Henson |
| 7,261,733 B1 | 8/2007 | Brown |
| 7,273,457 B2 | 9/2007 | Penner |
| 7,284,442 B2 | 10/2007 | Fleischman |
| 7,290,454 B2 | 11/2007 | Liu |
| 7,347,822 B2 | 3/2008 | Brockway |
| 7,347,826 B1 | 3/2008 | Karicherla |
| 7,353,711 B2 | 4/2008 | ODowd et al. |
| 7,370,121 B2 | 5/2008 | Khandelwal |
| 7,425,200 B2 | 9/2008 | Brockway |
| 7,432,723 B2 | 10/2008 | Ellis |
| 7,466,120 B2 | 12/2008 | Miller |
| 7,483,805 B2 | 1/2009 | Sparks |
| 7,498,799 B2 | 3/2009 | Allen |
| 7,519,325 B2 | 4/2009 | Wakim |
| 7,550,978 B2 | 6/2009 | Joy |
| 7,566,308 B2 | 7/2009 | Stahmann |
| 7,574,792 B2 | 8/2009 | OBrien et al. |
| 7,641,619 B2 | 1/2010 | Penner |
| 7,647,831 B2 | 1/2010 | Corcoran |
| 7,666,151 B2 | 2/2010 | Sullivan |
| 7,679,355 B2 | 3/2010 | Allen |
| 7,686,762 B1 | 3/2010 | Najafi |
| 7,686,768 B2 | 3/2010 | Bodecker |
| 7,839,153 B2 | 11/2010 | Joy |
| 7,932,732 B2 | 4/2011 | Ellis et al. |
| 7,936,174 B2 | 5/2011 | Ellis |
| 7,973,540 B2 | 7/2011 | Kroh et al. |
| 8,014,865 B2 | 9/2011 | Najafi et al. |
| 8,104,358 B1 | 1/2012 | Jia et al. |
| 8,111,150 B2 | 2/2012 | Miller et al. |
| 8,118,748 B2 | 2/2012 | Schugt et al. |
| 8,154,389 B2 | 4/2012 | Rowland |
| 8,159,348 B2 | 4/2012 | Ellis |
| 8,237,451 B2 | 8/2012 | Joy et al. |
| 8,271,093 B2 | 9/2012 | Von Arx |
| 8,360,984 B2 | 1/2013 | Yadav |
| 8,373,559 B2 | 2/2013 | McCain |
| 8,384,524 B2 | 2/2013 | Cobianu |
| 8,424,388 B2 | 4/2013 | Mattes et al. |
| 8,432,265 B2 | 4/2013 | Rowland |
| 8,493,187 B2 | 7/2013 | Rowland |
| 8,512,252 B2 | 8/2013 | Ludomirsky et al. |
| 8,565,866 B2 | 10/2013 | Lomqvist et al. |
| 8,570,186 B2 | 10/2013 | Nagy |
| 8,665,086 B2 | 3/2014 | Miller et al. |
| 8,669,770 B2 | 3/2014 | Cros |
| 8,700,924 B2 | 4/2014 | Mian et al. |
| 8,852,099 B2 | 10/2014 | Von Arx |
| 8,866,788 B1 | 10/2014 | Birnbaum |
| 8,870,787 B2 | 10/2014 | Yadav et al. |
| 8,901,775 B2 | 12/2014 | Armstrong et al. |
| 9,044,150 B2 | 6/2015 | Brumback |
| 9,089,717 B2 | 7/2015 | Forsell |
| 9,265,428 B2 | 2/2016 | OBrien et al. |
| 9,305,456 B2 | 4/2016 | Rowland |
| 9,489,831 B2 | 11/2016 | Nagy |
| 9,496,924 B2 | 11/2016 | Aber et al. |
| 9,498,130 B2 | 11/2016 | Najafi et al. |
| 9,712,894 B2 | 7/2017 | Lee et al. |
| 9,721,463 B2 | 8/2017 | Rowland |
| 9,723,997 B1 | 8/2017 | Lamego |
| 9,839,732 B2 | 12/2017 | Armstrong et al. |
| 9,867,552 B2 | 1/2018 | Rowland |
| 9,894,425 B2 | 2/2018 | Nagy |
| 10,022,054 B2 | 7/2018 | Najafi et al. |
| 10,105,103 B2 | 10/2018 | Goldshtein et al. |
| 10,143,388 B2 | 12/2018 | Cros et al. |
| 10,205,488 B2 | 2/2019 | Hershko et al. |
| 10,307,067 B1 | 6/2019 | Xu |
| 10,383,575 B2 | 8/2019 | Najafi et al. |
| 10,478,067 B2 | 11/2019 | Najafi |
| 10,687,709 B2 | 6/2020 | Najafi |
| 10,687,716 B2 | 6/2020 | Goldshtein et al. |
| 10,709,341 B2 | 7/2020 | White et al. |
| 10,874,349 B2 | 12/2020 | Goldshtein et al. |
| 10,874,479 B2 | 12/2020 | Forsell |
| 11,154,207 B2 | 10/2021 | Campbell et al. |
| 11,206,988 B2 | 12/2021 | Goldshtein et al. |
| 2002/0045921 A1 | 4/2002 | Wolinsky |
| 2002/0072656 A1 | 6/2002 | Vantassel |
| 2002/0115920 A1 | 8/2002 | Rich |
| 2002/0138009 A1 | 9/2002 | Brockway |
| 2002/0151816 A1 | 10/2002 | Rich |
| 2002/0177782 A1 | 11/2002 | Penner |
| 2002/0188207 A1 | 12/2002 | Richter |
| 2003/0062957 A1 | 4/2003 | Terashima |
| 2003/0136417 A1 | 7/2003 | Fonseca |
| 2003/0139677 A1 | 7/2003 | Fonseca |
| 2003/0139771 A1 | 7/2003 | Fisher |
| 2003/0158584 A1 | 8/2003 | Cates |
| 2003/0191496 A1 | 10/2003 | Edwards |
| 2004/0102806 A1 | 5/2004 | Broome |
| 2004/0158138 A1 | 8/2004 | Kilcoyne |
| 2004/0172446 A1 | 9/2004 | Dorman |
| 2004/0220637 A1 | 11/2004 | Zdeblick |
| 2004/0239504 A1 | 12/2004 | Kalinin |
| 2004/0255643 A1 | 12/2004 | Wise |
| 2004/0260164 A1 | 12/2004 | Kilcoyne |
| 2005/0013685 A1 | 1/2005 | Ricketts |
| 2005/0015014 A1 | 1/2005 | Fonseca |
| 2005/0025322 A1 | 2/2005 | Henson |
| 2005/0043601 A1 | 2/2005 | Kilcoyne |
| 2005/0049634 A1 | 3/2005 | Chopra |
| 2005/0080346 A1 | 4/2005 | Gianchandani |
| 2005/0090719 A1 | 4/2005 | Scheiner |
| 2005/0103114 A1 | 5/2005 | Bly |
| 2005/0145187 A1 | 7/2005 | Gray |
| 2005/0154321 A1 | 7/2005 | Wolinsky |
| 2005/0160825 A1 | 7/2005 | Zdeblick |
| 2005/0160827 A1 | 7/2005 | Zdeblick |
| 2005/0187482 A1 | 8/2005 | O'Brien |
| 2005/0201178 A1 | 9/2005 | Ho |
| 2005/0228308 A1 | 10/2005 | Iddan |
| 2005/0287287 A1 | 12/2005 | Parker |
| 2005/0288596 A1 | 12/2005 | Eigler |
| 2005/0288604 A1 | 12/2005 | Eigler |
| 2005/0288722 A1 | 12/2005 | Eigler |
| 2006/0052821 A1 | 3/2006 | Abbott |
| 2006/0064133 A1 | 3/2006 | Von Arx |

(56) References Cited

U.S. PATENT DOCUMENTS

| | | |
|---|---|---|
| 2006/0064134 A1 | 3/2006 | Mazar |
| 2006/0064142 A1 | 3/2006 | Chavan |
| 2006/0064143 A1 | 3/2006 | Von Arx |
| 2006/0085039 A1 | 4/2006 | Hastings |
| 2006/0107749 A1 | 5/2006 | Liu |
| 2006/0116590 A1 | 6/2006 | Fayram |
| 2006/0117859 A1 | 6/2006 | Liu |
| 2006/0122522 A1 | 6/2006 | Chavan |
| 2006/0129050 A1 | 6/2006 | Martinson |
| 2006/0144155 A1 | 7/2006 | Liu |
| 2006/0161171 A1 | 7/2006 | Schwartz |
| 2006/0177956 A1 | 8/2006 | O'Brien |
| 2006/0178583 A1 | 8/2006 | Montegrande |
| 2006/0178695 A1 | 8/2006 | Decant |
| 2006/0196277 A1 | 9/2006 | Allen |
| 2006/0206146 A1 | 9/2006 | Tenerz |
| 2006/0212047 A1 | 9/2006 | Abbott |
| 2006/0217762 A1 | 9/2006 | Meahs |
| 2006/0217763 A1 | 9/2006 | Abbott |
| 2006/0217764 A1 | 9/2006 | Abbott |
| 2006/0219022 A1 | 10/2006 | Ohta |
| 2006/0229488 A1 | 10/2006 | Ayre |
| 2006/0241354 A1 | 10/2006 | Allen |
| 2006/0244465 A1 | 11/2006 | Kroh |
| 2006/0247724 A1 | 11/2006 | Gerber |
| 2006/0271078 A1 | 11/2006 | Modesitt |
| 2006/0287602 A1 | 12/2006 | O'Brien |
| 2006/0287700 A1 | 12/2006 | White |
| 2007/0007240 A1 | 1/2007 | Wise |
| 2007/0028698 A1 | 2/2007 | Guziak |
| 2007/0049980 A1 | 3/2007 | Zielinski |
| 2007/0049984 A1 | 3/2007 | Osypka |
| 2007/0060959 A1 | 3/2007 | Salo |
| 2007/0061089 A1 | 3/2007 | Liu |
| 2007/0073351 A1 | 3/2007 | Zielinski |
| 2007/0074579 A1 | 4/2007 | Cook |
| 2007/0088388 A1 | 4/2007 | Opolski |
| 2007/0096715 A1 | 5/2007 | Joy |
| 2007/0100215 A1 | 5/2007 | Powers |
| 2007/0106246 A1 | 5/2007 | Modesitt |
| 2007/0106328 A1 | 5/2007 | Wardle |
| 2007/0106333 A1 | 5/2007 | Fernandez |
| 2007/0112358 A1 | 5/2007 | Abbott |
| 2007/0118039 A1 | 5/2007 | Bodecker |
| 2007/0142727 A1 | 6/2007 | Zhang |
| 2007/0149880 A1 | 6/2007 | Willis |
| 2007/0157734 A1 | 7/2007 | Skwara |
| 2007/0160748 A1 | 7/2007 | Schugt |
| 2007/0191717 A1 | 8/2007 | Rosen |
| 2007/0197957 A1 | 8/2007 | Hunter |
| 2007/0210786 A1 | 9/2007 | Allen |
| 2007/0261497 A1 | 11/2007 | O'Brien |
| 2007/0274565 A1 | 11/2007 | Penner |
| 2007/0282210 A1 | 12/2007 | Stern |
| 2008/0015421 A1 | 1/2008 | Penner |
| 2008/0033527 A1 | 2/2008 | Nunez |
| 2008/0058632 A1 | 3/2008 | Tai |
| 2008/0082005 A1 | 4/2008 | Stern |
| 2008/0125647 A1* | 5/2008 | Rosengren ............. A61B 34/20 600/424 |
| 2008/0215460 A1 | 9/2008 | McKibben |
| 2008/0258930 A1* | 10/2008 | Demichele ............. A61B 90/90 340/691.1 |
| 2008/0281212 A1 | 11/2008 | Nunez |
| 2008/0284599 A1* | 11/2008 | Zdeblick .............. A61B 5/4839 340/572.1 |
| 2009/0115396 A1 | 5/2009 | Allen |
| 2009/0224773 A1 | 9/2009 | Joy |
| 2009/0224837 A1 | 9/2009 | Joy |
| 2010/0026318 A1 | 2/2010 | Kroh |
| 2010/0039234 A1 | 2/2010 | Soliven |
| 2010/0161004 A1 | 6/2010 | Najafi |
| 2010/0294937 A1 | 11/2010 | Finch |
| 2011/0087306 A1* | 4/2011 | Goossen ............. A61N 1/3718 607/60 |
| 2012/0296234 A1 | 11/2012 | Wilhelm |
| 2013/0072747 A1* | 3/2013 | Mashiach ............ A61N 1/0548 607/42 |
| 2013/0331036 A1 | 12/2013 | Baker |
| 2014/0187889 A1* | 7/2014 | Cohen .................. A61B 5/1495 600/365 |
| 2014/0257058 A1 | 9/2014 | Clarysse |
| 2014/0306807 A1 | 10/2014 | Rowland |
| 2015/0223751 A1* | 8/2015 | Zdeblick .............. A61B 5/4839 600/302 |
| 2016/0045137 A1 | 2/2016 | Axelrod |
| 2016/0310077 A1* | 10/2016 | Hunter ..................... A61C 8/00 |
| 2017/0023542 A1 | 1/2017 | Wang |
| 2017/0061168 A1 | 3/2017 | Sundaram |
| 2017/0224248 A1* | 8/2017 | Zou ........................ A61B 5/061 |
| 2018/0199849 A1 | 7/2018 | Axelrod |
| 2020/0022601 A1 | 1/2020 | Rogers et al. |
| 2020/0297218 A1 | 9/2020 | White et al. |
| 2021/0068681 A1 | 3/2021 | Campbell et al. |
| 2021/0275733 A1 | 9/2021 | Goldshtein et al. |

FOREIGN PATENT DOCUMENTS

| | | |
|---|---|---|
| JP | 2007210547 | 8/2007 |
| WO | WO/2005/107583 | 11/2005 |
| WO | WO2006096582 | 9/2006 |
| WO | WO/2006/130488 | 12/2006 |
| WO | WO2010042055 | 4/2010 |
| WO | WO2010117356 | 10/2010 |
| WO | WO2012149008 | 11/2012 |
| WO | WO20131842583 | 12/2013 |
| WO | 2014170771 A1 | 10/2014 |
| WO | 2017025300 | 2/2017 |
| WO | WO2017025300 | 2/2017 |
| WO | 2017115112 | 7/2017 |

OTHER PUBLICATIONS

The International Bureau of WIPO, International Search Report and Written Opinion of International Searching Authority, dated Aug. 4, 2008, International Application No. PCT/US08/03475.

International Search Authority, The International Search Report and The Written Opinion, dated Jun. 30, 2009, International Application No. PCT/US2009/039730.

Extended European Search Report, Endotronix, Inc., Application No. 10762085.8-2319/2417590, dated Jan. 4, 2013.

International Preliminary Report on Patentability, Endotronix, Inc., PCT/US2012/034979, dated Nov. 7, 2013.

International Search Report and the Written Opinion of the International Searching Authority, Endotronix, Inc., PCT/US2012/34979, dated Nov. 2, 2012.

International Search Report, dated Nov. 14, 2008, for corresponding PCT patent application No. PCT/US2008/069217 filed Jul. 3, 2008 (4 pages).

Nagumo, J., Uchiyama, A. Kimoto, S., Watanuki, T., Hori, M., Suma, K., Ouchi, A., Kumano, M., and Watanabe, H., Echo Capsule for Medical Use (A Batteryless Endoradiosonde), IRE Transaction on Bio-Medical Electronics, pp. 195-199, 1962.

Haynes, H.E. & Witchey, A.L., Medical Electronics; The Pill That "Talks" DEP, 1960, pp. 52-54, Cambden, NJ.

Collins, Carter, Miniature Passive Pressure Transenor for Implanting in the Eye, Transactions on Bio-Medical Engineering, vol. BME-14, No. 2, pp. 74-83, Apr. 1967.

European Patent Office, Extended European Search Report, Application No. 17000257.0, dated Jun. 14, 2017.

International Searching Authority, European Patent Office; International Search Report and Written Opinion for International Application No. PCT/US2018/019475; dated May 22, 2018.

* cited by examiner

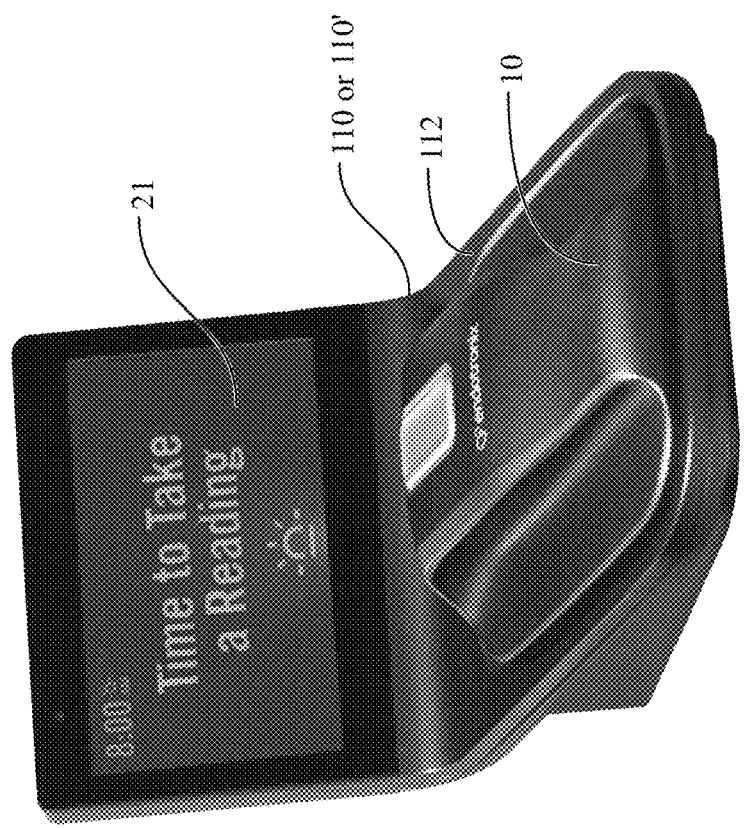
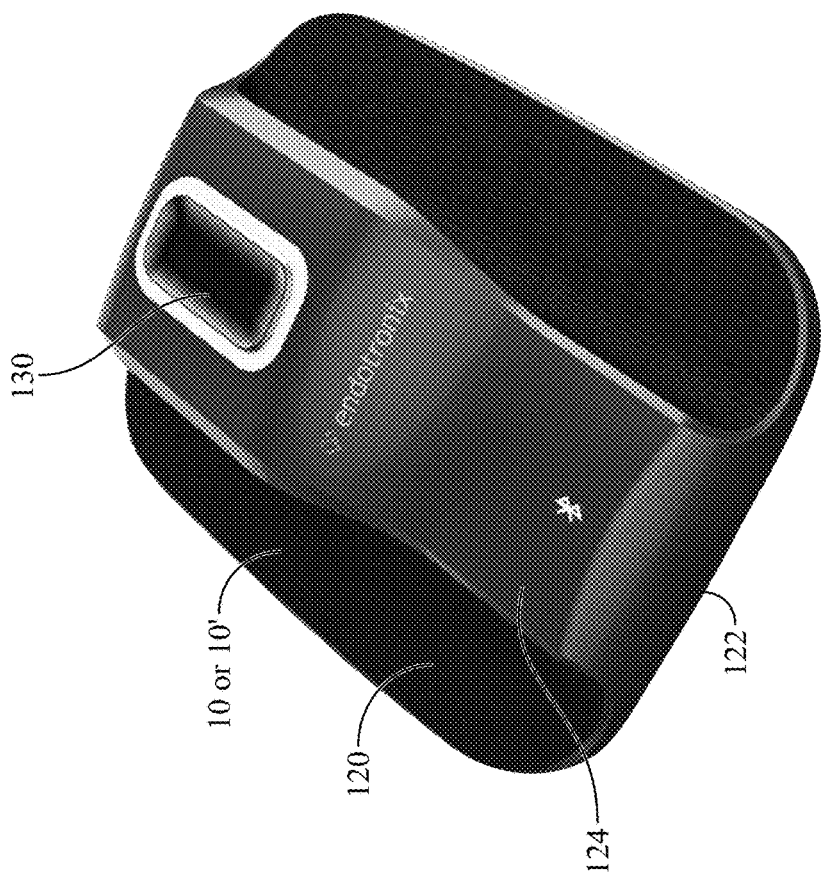
FIG. 4
FIG. 3

METHOD FOR COMMUNICATING WITH IMPLANT DEVICES

CROSS-REFERENCE TO RELATED APPLICATIONS

This application claims the benefit of and priority to U.S. Provisional Patent App. No. 62/956,686 filed on Jan. 3, 2020 and is a continuation-in-part of U.S. Utility patent application Ser. No. 16/588,192 entitled WIRELESS SENSOR READER ASSEMBLY and filed on Sep. 30, 2019, which is a continuation of U.S. Utility patent application Ser. No. 15/903,809 entitled WIRELESS SENSOR READER ASSEMBLY and filed on Feb. 23, 2018, now U.S. Pat. No. 10,430,624, which claims priority to U.S. Provisional Patent App. No. 62/463,203 entitled "WIRELESS SENSOR READER ASSEMBLY" and filed on Feb. 24, 2017, each of which are hereby incorporated by reference in their entireties.

TECHNICAL FIELD

This disclosure relates generally to providing a method for replacing an external reader device configured for communication with an implant that is currently located within the body of a patient. More particularly, this disclosure is related to providing a replacement external device and system for wirelessly interacting with an existing implanted device to communicate information between the implant and the system.

BACKGROUND

The treatment of end stage diseases such as heart failure, kidney disease, pulmonary disease, liver disease is changing. Traditional methods included waiting for a patient to have an acute symptomatic episode (often a medical emergency), hospitalizing them, treating the symptoms, and then sending them home with new medications or an implanted or wearable device. However, these methods generally do not monitor the patient's health status at home on an ongoing basis using communication tools such as internet connectivity. Further, they do not monitor the patient's compliance with prescribed therapy, for example taking medication or using a device properly. Often, interaction between the patient and the clinic does not take place until the next acute symptomatic episode.

Current methods have incorporated long term care for chronic disease management for heart failure patients. These methods include providing a dedicated physician, often a cardiologist, to be responsible for care of a patient's heart failure for the rest of that patient's life. The physician and their staff may use technology such as a home monitoring system such as disclosed by commonly owned U.S. patent application Ser. No. 16/040,034 incorporated by reference herein to communicate with and receive daily data from the patient at home. Medical staff may use the data to continuously treat the patient. As a patient's health worsens to a level where a device is warranted, such as an implant to measure pulmonary artery pressure, the physician prescribes the device and the patient may be implanted with a system described in the following patents: U.S. Pat. Nos. 7,245,117; 8,154,389; 8,493,187; 8,432,265; and 8,570,186. This model may be more clinically effective and better economically for treating heart failure.

FIGS. 1 and 2 illustrate a known reader device 10 that may be configured to remotely and wirelessly communicate with an implant device 12. The implant device 12 may include a sensor that may be a wireless and a passive type sensor. To initiate communication, the reader device 10 may be placed in proximity to the implant device 12 and be capable of exciting the sensor by transmitting a signal 14 (excitation pulse), such as a radio frequency ("RF") pulse, at or near the resonant frequency of the implant device 12. Note that as used herein, "excitation" pulse is any signal 14 transmitted from the reader to the sensor, that evinces a response signal 16 from the sensor. For passive sensors with no internal energy storage, the excitation signal 14 may power the implant device 12, enabling it to emit a response signal 16. For active sensors with internal energy storage, the excitation pulse may be a data signal only. As used herein, "excitation", "stimulus" or "stimulating signal" are used interchangeably. An "energizing" signal may be a subset of an excitation signal that transfers power to the sensor. After the excitation pulse 14 is extinguished, the implant device 12 may emit a response signal 16 for a short period of time in response to the signal/excitation pulse 14 from the reader device 10. In particular, the implant device 12 may be designed to be placed within the cardiovascular system of a human to provide a signal that may be a function of a sensed parameter (such as blood pressure) that is desirable to be identified. The reader device 10 may be configured to receive and ascertain the frequency of the response signal 16 via wireless communication with the implant device 12 and extrapolate the sensed parameter. In another embodiment, the excitation signal 14 may be a continuous signal that is not extinguished prior to receiving response signal 16. In this embodiment, excitation signal 14 and response signal 16 may continue simultaneously, and may be set at different frequencies to avoid mutual interference. The energizing signal 14 may comprise electrical, magnetic, ultrasonic, mechanical, optical, acoustic, or any other type of wireless energy transfer known in the art.

The implant device 12 may also be an active sensor, powered by an energy storage device such as battery, or an energy harvesting system as are known in the art, which does not require a power pulse to be transmitted from the reader device 10, but may respond to a data stimulus or excitation signal 14 from reader device 10. The implant device 12 may also communicate via a digital or analog wireless signal using any of the many modulation schemes well-known in the art. The term "battery" as used herein refers to any type of electrochemical energy storage device. A "battery" may have one or more cells, and may be a primary (non-rechargeable) or secondary (rechargeable) type.

These known reader devices 10 are calibrated for proper communication with the implant device prior to the implant device 12 being placed within a patient. This allows known reader devices 10 to properly communicate with the implant device 12 after it is implanted within a patient. As illustrated by FIG. 1, the reader device 10 may also communicate with background infrastructure to process the data and communicate with the various devices. The background infrastructure may include a data interface 17. The reader device 10 and data interface 17 may be connected wirelessly, and may be physically distant from one another. The reader device 10 may send information, such as data related to the implant device 12 to the data interface 17. The reader device 10 may further send information regarding the status of the reader device 10 to the data interface 17. The data interface 17 may provide configuration information to the reader device 10. For example, the data interface 17 may provide information regarding schedules and intervals for sampling or communicating with the implant device 12.

The background infrastructure may also include a data gathering system 18 in which the data interface 17 may communicate with the data gathering system 18 to exchange status and control signals, as well as provide sensor data. The remote data system 18 may include a data gathering module 19 to receive data from the data interface 17, a data logging module 20 to store the received data, and a data display 21 to display the implant device data. In one embodiment, the reader 10 may upload raw frequency data obtained from implant device 12 to data interface 17. Data interface 17 may in turn upload the raw data to data gathering system 18, which uses stored calibration coefficients and preset algorithms to process the raw frequency data and convert it to the parameter of interest. Data gathering system 18 may further use identification data from the reader 10 or implant device 12 to associate the processed data with a given user, based on a pre-loaded associative database. In an embodiment, data interface 17 may be a device that accepts raw frequency data and formats it for uploading via transmission control protocol/internet protocol (TCP/IP) to the internet. Further, data gathering system 18 may reside on a remote server on the internet, and may make its processed, associated data available to authorized users, such as clinicians responsible for care of the patient taking the data at home. The data transfers in this embodiment may occur in real time or after initial raw data acquisition by the reader 10.

The reader device 10 and implant device 12 may be part of a larger system of devices, which work together to measure a parameter from inside a patient's body, and communicate the results of the measurement to medical personnel at a clinic, as depicted schematically in FIG. 5.

In a typical cardiology practice that has adopted this monitoring system model, a team comprising a physician such as a cardiologist and related clinical staff may be caring for several hundred patients or even more. A portion of those patients may be prescribed the described implant to monitor implant data which may be provided on a subscription basis. Here a clinic may pay to the monitoring system provider a monthly fee to obtain the implant data (such as pulmonary artery pressure data and other patient related data) by an internet connection as received from the patient at their homes. The clinic may recoup their subscription fee by billing Medicare for "Chronic Care Management."

In a typical practice, new patients are continuously being identified as being candidates for an implant. So there is a continuous pipeline of implanted patients who are being monitored, and new ones receiving implants. A clinician may select various different home monitoring systems along this model provided by various entities such as the CardioMEMS® product by Abbott or the Cordella® product by Endotronix. The available home monitoring systems operate on the general model outlined above, wherein one clinical staff team manages a number of heart failure patients using pulmonary artery pressure data. However, each commercial system includes an implant device 12 that can only communicate with that system's specific external reader device 10 and related software and hardware infrastructure associated with those devices. This may be primarily due to the different implants having various electronic characteristics such as: full scale frequency range, sensitivity (frequency change per unit pressure change), and RF Quality Factor (Q).

FIG. 5 illustrates a diagram of an existing health monitoring system while FIG. 6 illustrates a typical commercial system for chronic care management involving an implantable device such as a sensor. The sensor 12 may be an implantable device identified as reference 12 in FIG. 5 and circle "D" (for "Device") in FIG. 6. These illustrations identify the practical steps for an implantable device 12 to be placed within a patient and to facilitate the transfer of information from the patient at home to the clinician. In this example, clinic 295 may be an outpatient center, meaning patients generally don't stay overnight but do go for evaluation and diagnosis. Hospital 210 may be an in-patient facility where patients may be admitted and may stay overnight. A clinic 295 and a hospital 210 might physically be different parts of the same building, but they often are not. Further, the same clinicians (typically doctors, nurses, and the like) may work in different roles at clinic and hospital; but more typically there are separate dedicated teams with different functions.

Referring now to FIG. 5, in the Hospital 210 a delivery catheter 220 may be used to place implant device 12 into the body of a patient. During the implant procedure, calibration equipment 230 may be used to calibrate the newly implanted device 12. The calibration equipment 230 may comprise a reader 10 as well as hardware and software for inputting a reference reading, which is taken by a known standard reference that measures the same parameter as implant device 10. The calibration equipment 230 may input readings by the newly implanted device 12 and its reader 10, as well as simultaneous or near-simultaneous readings taken by the known standard reference device. Inputs may be hardwired, wireless, or manually entered by staff. The calibration equipment 230 may use the device 12 reading and the simultaneous reference reading to mathematically generate calibration coefficients that may be applied to future raw data created by that sensor 12/reader 10 pair. The calibration equipment 230 may also obtain calibration data from the factory 280 related to sensor 12 and reader 10 to factor into its calibration coefficient generating algorithm. Database and processor 240 may be used to store, process or transfer such data between the factory 280 and the calibration equipment 230 located in the Hospital 210. The calibration data taken during implantation may also be transferred from calibration equipment 230 to database and processor 240 and may be further transferred to factory database 280. After implantation and discharge from Hospital 210, the patient may then take the reader 10 to her/his home 250 wherein the reader 10 may be used to communicate with the implant device 12 and may transmit raw reader data to a hub 110 located proximate to the patient and preferably at the patient's home or residence 250. The hub 110 may be a computer device that is programmed to include a software application 270 that is configured to communicate raw reader data or processed reader data to the database and processor 240 associated with the background infrastructure of the reader/implant system of the first party or entity.

The database and processor 240 may include an algorithm or logic that may carry out one or more of the following functions for processing raw data: filtering; averaging; removing invalid data points according to preset criteria; conversion to final output using calibration data; authentication; validation; sanity checking; association with a known hub 260; compression/decompression; conditioning based on historical data (learning algorithms), and associating the data with a given patient. Besides sensed data, the reader device 10 and hub 260 may communicate other information such as hardware and software configuration and identification data, reader device diagnostics (device internal or external temperatures, battery life, battery status, number of charge cycles, watchdog circuit logs, error logs, usage logs, self-test results, ambient Electromagnetic Interference (EMI), etc.), patient position (based on a tilt sensor 28 on the reader device 10), ambient pressure, sensor signal strength, ambient conditions such as temperature or humidity, software notifications or alerts, and usage or event logs. Further, reader 10 may communicate results of self-test data as described in commonly owned U.S. patent application Ser. No. 14/842,973 which is hereby incorporated by reference in its entirety. Still further, reader 10 may communicate other data from additional sensors built into it, including any of: an audio microphone acting as a stethoscope to detect rales, heart sounds, or other audible signals; an accelerometer for sensing shocks due to drops; an accelerometer for sensing shaking hands (for handheld versions of reader 10). The database 240 may store this data and make it available to the factory 280. The database 240 may store the raw data as well as the processed data and calibration data to allow other processing to be performed on the raw data in the future.

The database 240 may communicate the raw data or the processed data to another database 290 that is accessible to authorized users at a clinic 295. The database 290 may interface with a plurality of clinics 295, and only allow each clinic to access data associated with that clinic's patients. The database 290 may be considered a portal, and further may interface with a clinic's existing electronic health record (EHR), also known as electronic medical record (EMR) database (not shown). The system may allow authorized clinic users to transfer sensor 12 related data to the EHR, as well as data in the EHR to database 290. Database 290 may store the processed data, or may display it graphically or in some other form. It may provide a search capability to users at the clinic 295. Users at clinic 295 may use the raw data or processed data to guide therapy for patients implanted with the wireless sensor 12. As indicated above, the reader device 10 may communicate with a remote data interface 17 to transfer data to database 240. This communication pairing between reader 10 and data interface 17 may be considered a wireless pairing using Bluetooth, Zigbee, Wifi, cellular, or another format that allows for transfer of raw data. Note that although two databases 240 and 290 are shown in the FIG. 5 embodiment, these could be combined into one database, or broken out into many using a variety of data structures, architectures, and implementations.

In a typical example (FIG. 6), a clinician prescribes implantable device 12 to a patient. The patient goes to hospital 210 and gets the implantable device 12 implanted by a surgeon. The patient, now with the implantable device 12, goes home with an external reader device 10 and a data upload device or hub 110, 260 (these items may be one device or several working together as illustrated by FIGS. 3 and 4). The patient may be directed to take readings from the implant device 12 using the reader device 10 at home and to upload, communicate or otherwise transmit the data to a data server or other type of data storage. The clinician or staff may access the data via a clinician portal or other means. In this instance, the clinician may be responsible for dozens or hundreds of patients on an ongoing basis. FIG. 6 illustrates the basic steps but there may exist variations and add-ons, as for example by the system disclosed by commonly owned U.S. patent application Ser. No. 16/040,034 which is hereby incorporated by reference in its entirety.

In this and other known systems, the reader device 10, and backend data system (including the data server, clinician portal and data upload device 110, 260 that come with the implant device 12 are proprietary relative to one another (i.e. both are provided as a system by a first entity) in that the implant device 12 may only function with the other components and systems shown in FIG. 5 that are provided by the same entity. The reader device 10 and associated backend infrastructure are generally provided to the patient as they leave the hospital after the implant device 12 has been surgically implanted. As the implanted device 12 may be long-term or permanent, the proprietary home-based reader 10 issued to the patient is the only type of reader that a patient can use for the rest of the implant device's useful life.

These known systems present problems in that the company or other entity that manufactures and supplies the implanted device, reader device, and backend infrastructure also has to ensure there is at least one (and preferably several) hospitals or clinics in the area that perform the surgical implantation as well as be compatible with associated procedures and data processing infrastructure. This infrastructure also must be able to be practically implemented with the business of the hospital or clinician as it must be recognized by payment processing plans including such as the patient's insurance or government. Further, the implant devices may be placed within the patient for a permanent or extended duration and the existing reader device may become lost, damaged or require maintenance. Implanted devices are typically unavailable to be easily accessed from within the patient for known calibration techniques.

Multiple versions of the implant system described above are available from different entities, such as commercial suppliers. While these competing systems provide the same basic diagnostic function, each supplier's reader 10 is only compatible with that supplier's implant 12. Thus, once a patient is implanted with one implant product sourced from one particular supplier/entity/vendor, his/her long term care management physician is typically constrained to only use only that supplier's reader device and associated backend system for the life of that patient. It would be highly advantageous for the physician to have the option to use one supplier's reader 10 and data backend 17 on patients already implanted with a second supplier's sensor 12. Examples of situations in which this option would be of benefit include: (i) one reader or database has technical advantages over the other, such as a portable reader, better accuracy, or better EMI immunity, better cybersecurity, a superior user interface for patient or clinician, better tech support, etc; (ii) a patient moves to a new geographic region where their implant 12's reader 10 or database 17 is not supported, for example due to internet limitations, electrical power compatibility, wireless regulations, business reasons, legal reasons, regulatory reasons, or network access; (iii) insurance changes mandate use of a specific supplier's device for that clinic or region; (iv) the supplier of a device discontinues the reader 10 and backend 17 for business or other reasons; (v) the supplier's reader 10 or backend 17 is recalled for safety or other reasons by a government authority such as the United States Food and Drug Administration (FDA); (vi) there is cost advantage to using one reader 10 and backend 17 versus the other. If a given physician already has patients in her/his cohort who are implanted with a sensor from supplier entity A, but wishes to implant future patients with supplier entity B's sensor, it would be advantageous for her/him to use supplier B's reader device and backend for all patients regardless of which implant they have, so that the clinic would only have to pay for and be trained on supplier B's reader and data backend. Additionally, if a clinician prefers the reader 10 or data backend 17 of supplier A but is in a geographic area or insurance network where available Hospitals 210 only implant supplier B's sensor 12, she/he may wish to use supplier A's reader with supplier B's sensor with new patients right from the day of implant.

As such, there is a need to provide a device, method, and system to allow compatibility between components of different entities, suppliers, or vendors such as to provide replacement reader devices compatible with existing implant devices, and respective health monitoring infrastructure. Specifically, there may be a need for a technical method that allows a patient already implanted with one version of the implant device to safely and effectively use a different entity's version of an external reader and related infrastructure including, data upload device, data backend, and user interfaces for both patient and clinician. These methods may include devices configured to obtain data from implantable sensors that perform the same general function. Finally, there is a need for a method that allows competing commercial or government entities to develop components that interface with other entities' already implanted sensors, in a manner that is effective, safe, and compliant with medical regulations for device development, sale, and use.

Development of a reader device 10 for reading a pre-existing implant 12 is particularly challenging given the highly regulated nature of medical device design, development, verification, validation, and approval for use in the open market. An additional challenge is presented if the developer does not have known valid samples of the pre-existing implant 12, with which to carry out bench and animal testing with prototype readers 10. This development must satisfy stringent regulatory requirements imposed on medical device development programs by bodies such as the FDA. Among other requirements, the developer must thoroughly demonstrate, typically with bench results, that any testing involving human subjects does not present safety risk to those subjects prior to commencing such testing (pre-clinical phase), and throughout the development program (clinical phase). Therefore, a further method is needed to carry out product development and testing of wireless readers 10 in a safe, effective, and legal manner, when a quantity of prototype sensors 12 are not readily available.

BRIEF DESCRIPTION OF THE DRAWINGS

Objects and advantages together with the operation of the invention may be better understood by reference to the following detailed description taken in connection with the following illustrations, wherein:

FIG. 3 illustrates an embodiment of a reader device;

FIG. 4 illustrates an embodiment of a docking station with reader device;

SUMMARY

Figure 1:
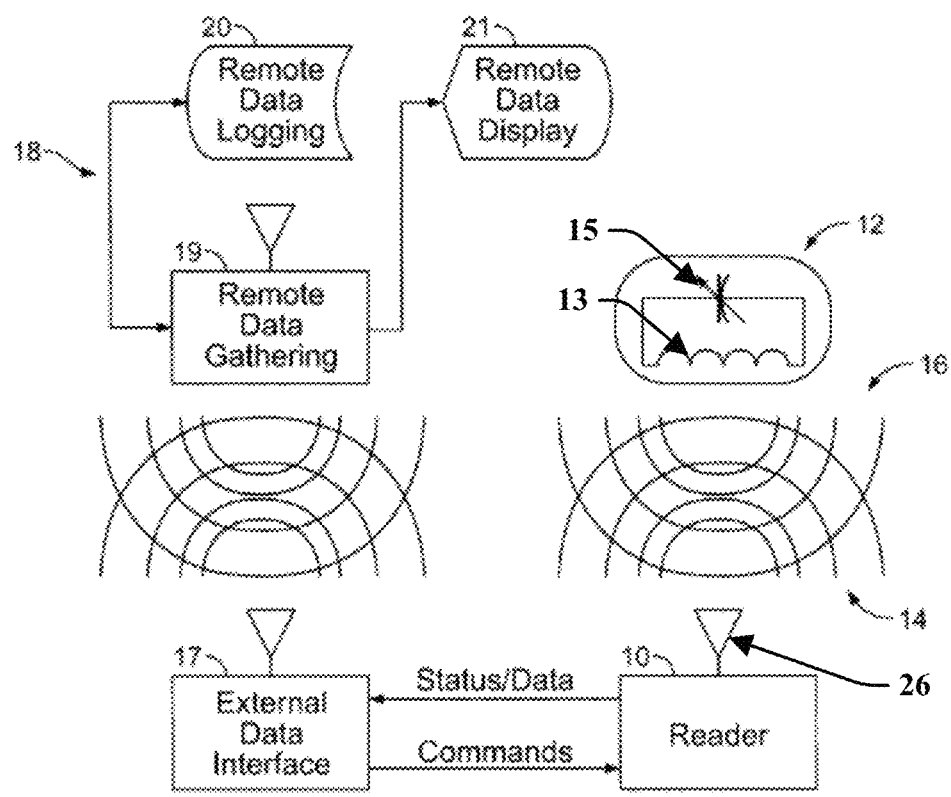
FIG. 1 illustrates a block diagram of a prior art passive wireless implant device and reader system.
Figure 2:
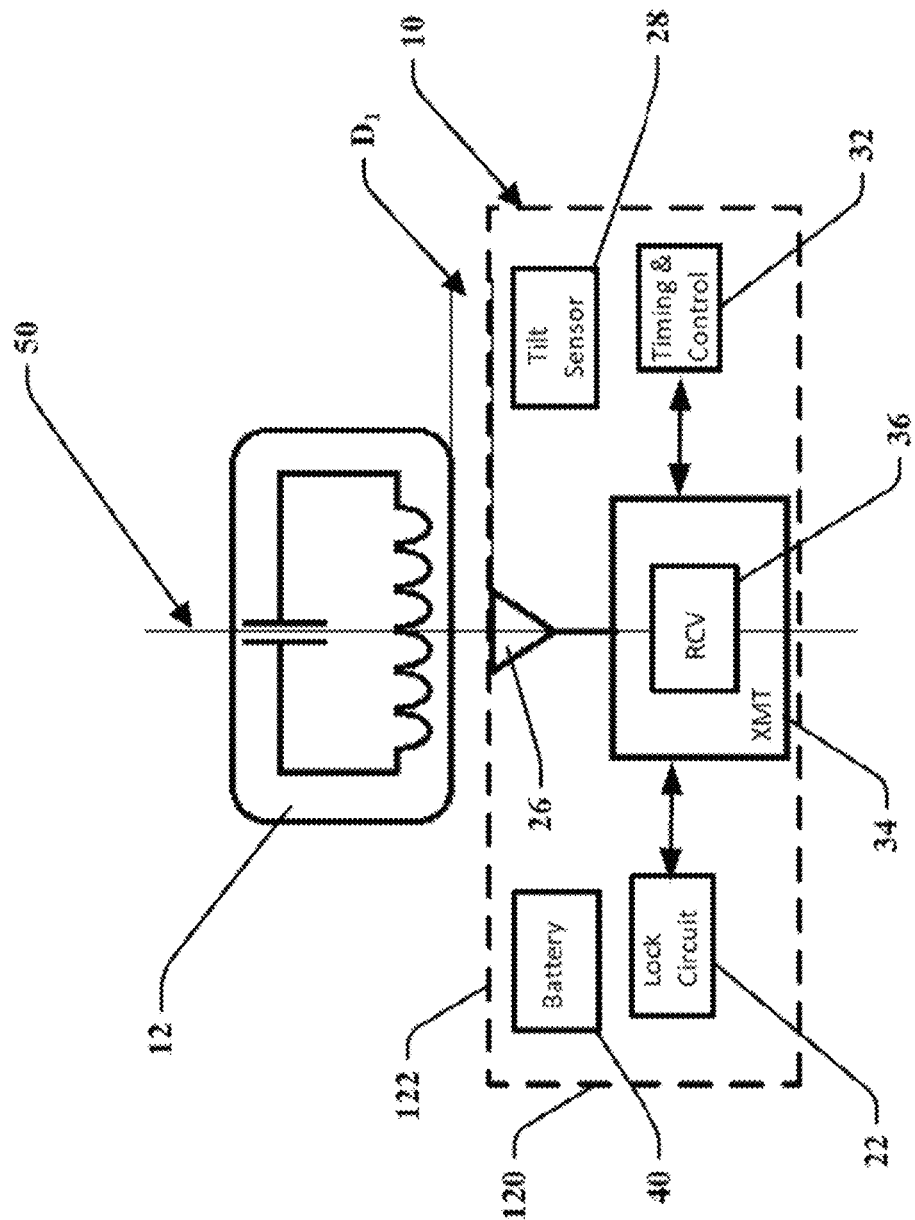
FIG. 2 illustrates an embodiment of an existing reader device and wireless implant device.
Figure 5:
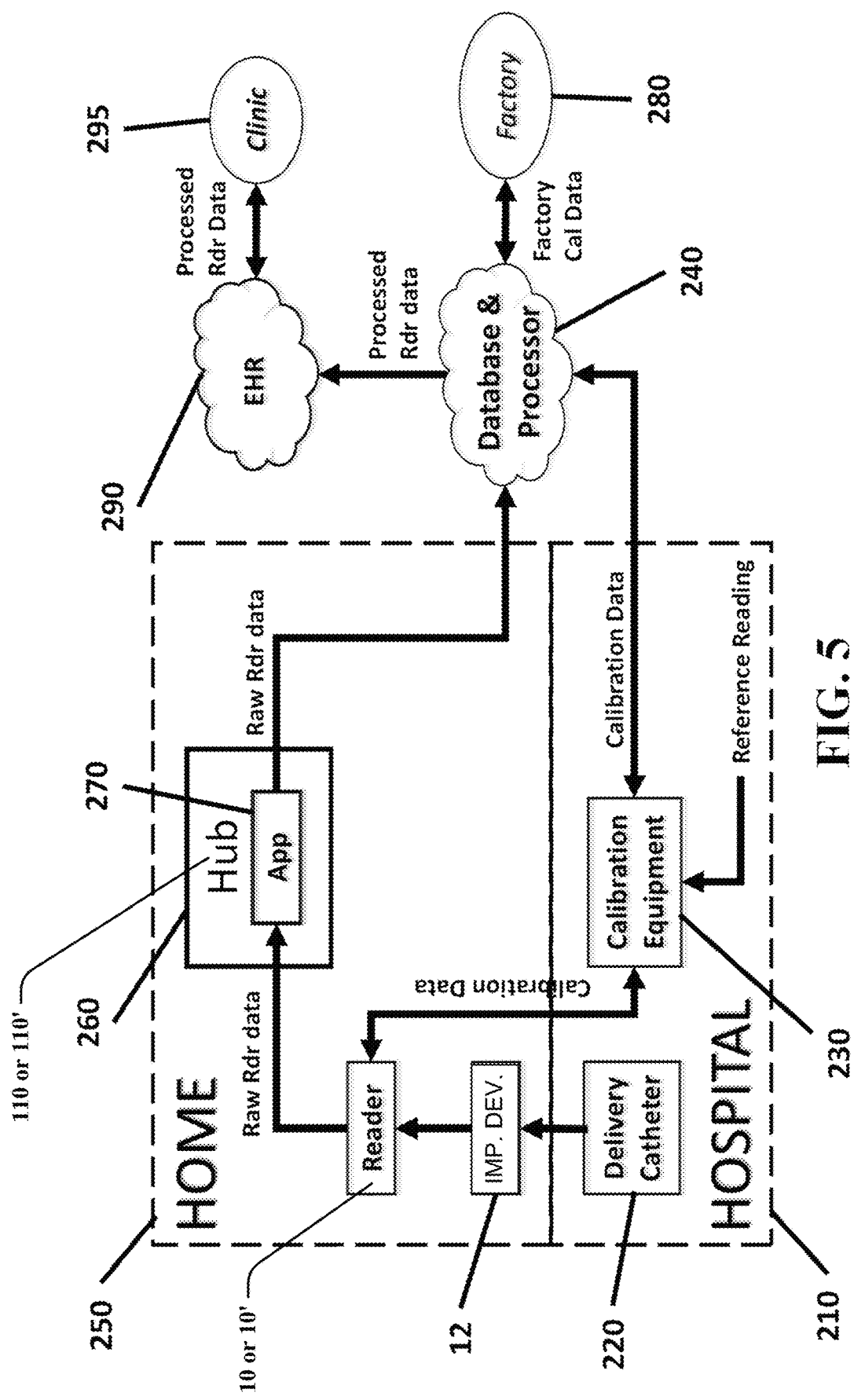
FIG. 5 illustrates a block diagram of an existing home monitoring system that includes a wireless implant device and reader system with related infrastructure.
Figure 6:
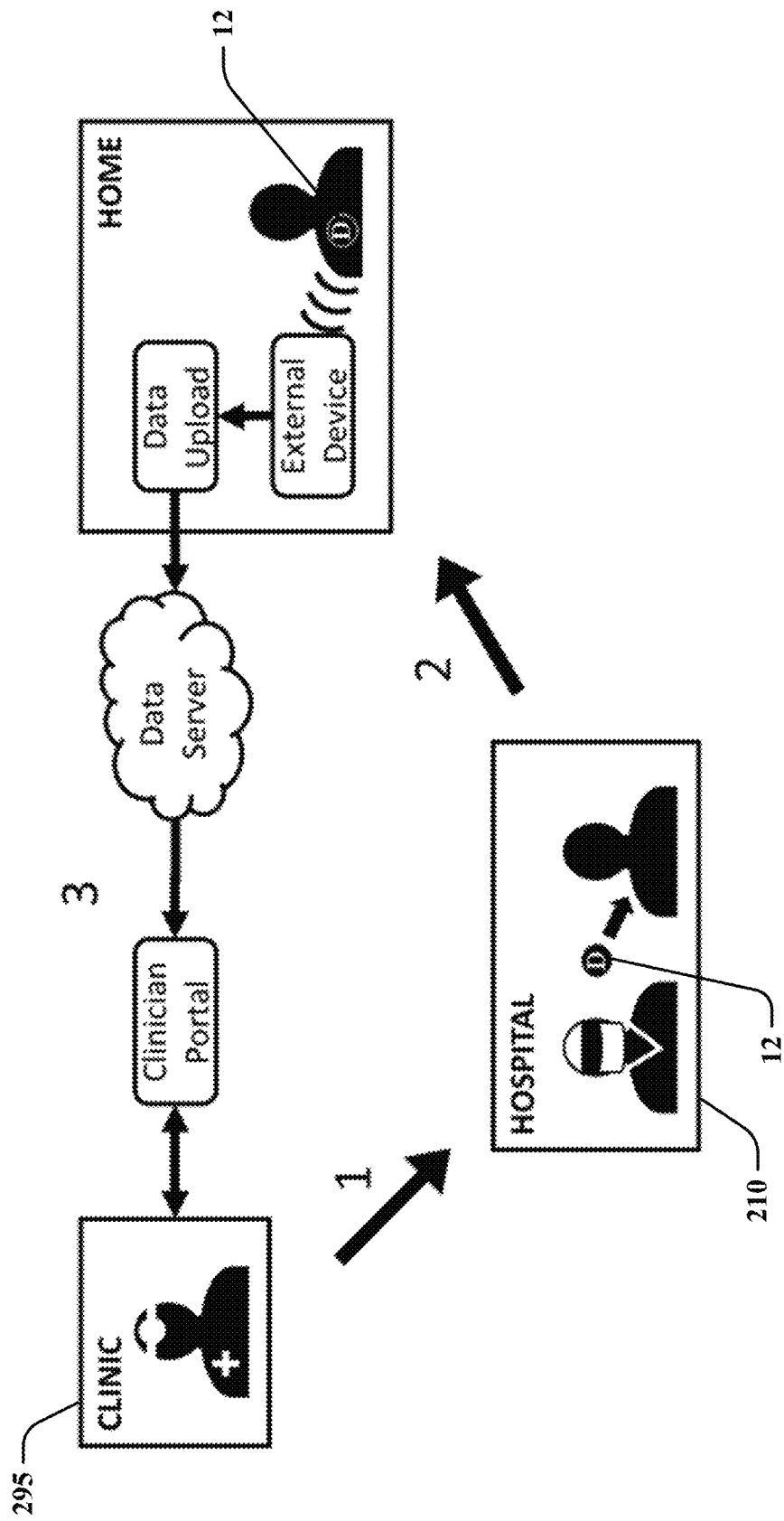
FIG. 6 is a schematic illustration of an existing patient data monitoring system.

Disclosed is a method for providing a device configured to wirelessly communicate energy, data, or commands with an implant device located within a human body, said method comprising the steps of: obtaining a first external device configured to wirelessly transfer energy, data, or commands to or from a first implant device, wherein said first external device communicates with the first implant device through a first proprietary protocol of a first entity; generating a plurality of first signals from said first external device; generating a plurality of output signals from said first implant device; characterizing said first signals and said output signals to determine input limits for said first implant device, said input limits being related to a range of signal outputs that have a reduced risk of harm to the patient; creating a second external device using said range of signal outputs from said first external device and said first implant device to communicate energy, data, or command signals between said second external device and said first implant device wherein said second external device is associated with a second entity. Regulatory approval may be obtained for said second external device and the second external device may be marketed to replace the first external devices for patients that have said first implant device associated with said first entity. Said first external device may be used to calibrate said second external device. Reimbursement approval may be obtained for payment said second external device from insurance providers. Said implant device may be at least one of a sensor and an actuator located in the cardiovascular system of a patient. Said implant device may be located in the pulmonary artery of said patient. Said implant device may be configured to sense pressure. Said implant device may comprise an LC resonant tank. Said implant device may be surgically implanted within said patient via a minimally invasive surgical procedure. Said implant device includes a glass housing having nitinol anchors. Said implant device may be configured to wirelessly receive or transmit digital or analog signals. Said implant device may be configured to provide a ring back signal having a frequency that corresponds to the measured value. Said implant device may be selected from at least one of: an electronic device, an optical device, a mechanical device, an ultrasonic device, a drug eluting device, a neurostimulation device, a cardiac pacing device, an electrocardiogram device, and a fibrillation monitor. Said implant device that is not already implanted in a human may be obtained to assist with generating a replacement external or reader device associated with the first entity.

In another embodiment, provided is a method for providing a clinician with physiological data obtained from a plurality of patients in remote locations, said method comprising: implanting a plurality of patients with a plurality of first implant devices that are operable with a plurality of first external devices, each of the first implant devices and the first external devices communicate via a first proprietary protocol of a first entity; providing each of said patients who have been implanted with said first implant device with said first external device for device operation at a home of the patient; identifying patients with a second implant device that provides physiological data wirelessly to a second external device, where said second implanted medical device is not operable with said first external device; developing a third external device that is operable with said second implanted medical device; providing at least one patient who is already implanted with said second medical device with said third external device for use at said home of the patient. Said first external device and said third external device may be configured to be operable with said first implant device and said second implant device to communicate physiological data. Said first and second implant devices include hardware and software used to aggregate, store, process, transmit, relay, format, packet, manage, and display said physiological data. Said third external device may be used in place of said second external device for patients that are already implanted with said second implant device associated with said second entity. Said third external device may be considered a 'replacement reader', replacing said second external device for a given patient. Said first external device may be used to calibrate said second external device. Reimbursement approval may be obtained for said third external device from insurance providers. Said implant device may be at least one of a sensor and an actuator that is located in the cardiovascular system of a patient. Said implant device may be located in the pulmonary artery of said patient. Said implant device may be configured to sense pressure. Said implant device may comprise an LC resonant tank. Said implant device may be surgically implanted within said patient via a minimally invasive surgical procedure. Said implant device may comprise a glass housing that includes nitinol anchors. Said implant device may be configured to wirelessly receive or transmit digital or analog signals. Said implant device may be configured to provide a ring back signal having a frequency that corresponds to a measured value. Said implant device may be selected from one of: an electronic device, an optical device, a mechanical device, an ultrasonic device, a drug eluting device, a neurostimulation device, a cardiac pacing device, an electrocardiogram device, and a fibrillation monitor. A sample of said second implant device that is not already implanted in a human may be obtained to assist with creating the third external device. Said third external device may also be configured to interoperate with the same backend data management system as said first external device and implant. Said third external device may have advantages over said second external device, such as being handheld, more accurate, or configured to be part of a larger measurement system that contains other diagnostic medical devices.

In another embodiment, provided is a method for creating a replacement reader device configured to replace a pre-existing reader device, wherein the replacement and pre-existing reader devices are configured to wirelessly communicate power, data, or commands to or from a separate device implanted within a human body, wherein said replacement reader device is operable with a system of devices to aggregate, store, process, transmit, relay, format, packet, manage, or display physiological data received from said third device implanted within a human body.

In yet another embodiment, provided is a system for providing a replacement reader device configured to replace an original reader device, wherein the replacement reader device and original reader device are configured to wirelessly communicate power, data, or commands to or from an implant device configured to be implanted within a human body, wherein said replacement reader device is operable with a system of devices to aggregate, store, process, transmit, relay, format, packet, manage, or display physiological data received from said implant device implanted within a human body. Said replacement reader device is configured to interoperate with a backend data management system associated with said original reader device and implant device implanted within a human body.

DETAILED DESCRIPTION

Reference will now be made in detail to exemplary embodiments, examples of which are illustrated in the accompanying drawings. It is to be understood that other embodiments may be utilized and structural and functional changes may be made. Moreover, features of the various embodiments may be combined or altered. As such, the following description is presented by way of illustration only and should not limit in any way the various alternatives and modifications that may be made to the illustrated embodiments.

As used herein, the words "example" and "exemplary" mean an instance, or illustration. The words "example" or "exemplary" do not indicate a key or preferred aspect or embodiment. The word "or" is intended to be inclusive rather an exclusive, unless context suggests otherwise. As an example, the phrase "A employs B or C," includes any inclusive permutation (e.g., A employs B; A employs C; or A employs both B and C). As another matter, the articles "a" and "an" are generally intended to mean "one or more" unless context suggests otherwise. As used herein, "entity" refers to any organization or group of organizations that provide implanted sensors and wireless external reader devices. It may be a commercial, institutional, or other organization, or a combination. The same organization could be the "first entity" in one context and the "second organization" in other contexts throughout this specification. Entities may be commercial competitors in the same market space.

A device, system, and method are provided for communicating between an implant such as a wireless sensor with a reader device. The reader device may be configured to communicate wirelessly with an implant device associated with a proprietary system of a particular entity, such as a first entity or a second entity. The communication herein may be described to be a proprietary communication protocol associated with that particular entity.

Figure 7:
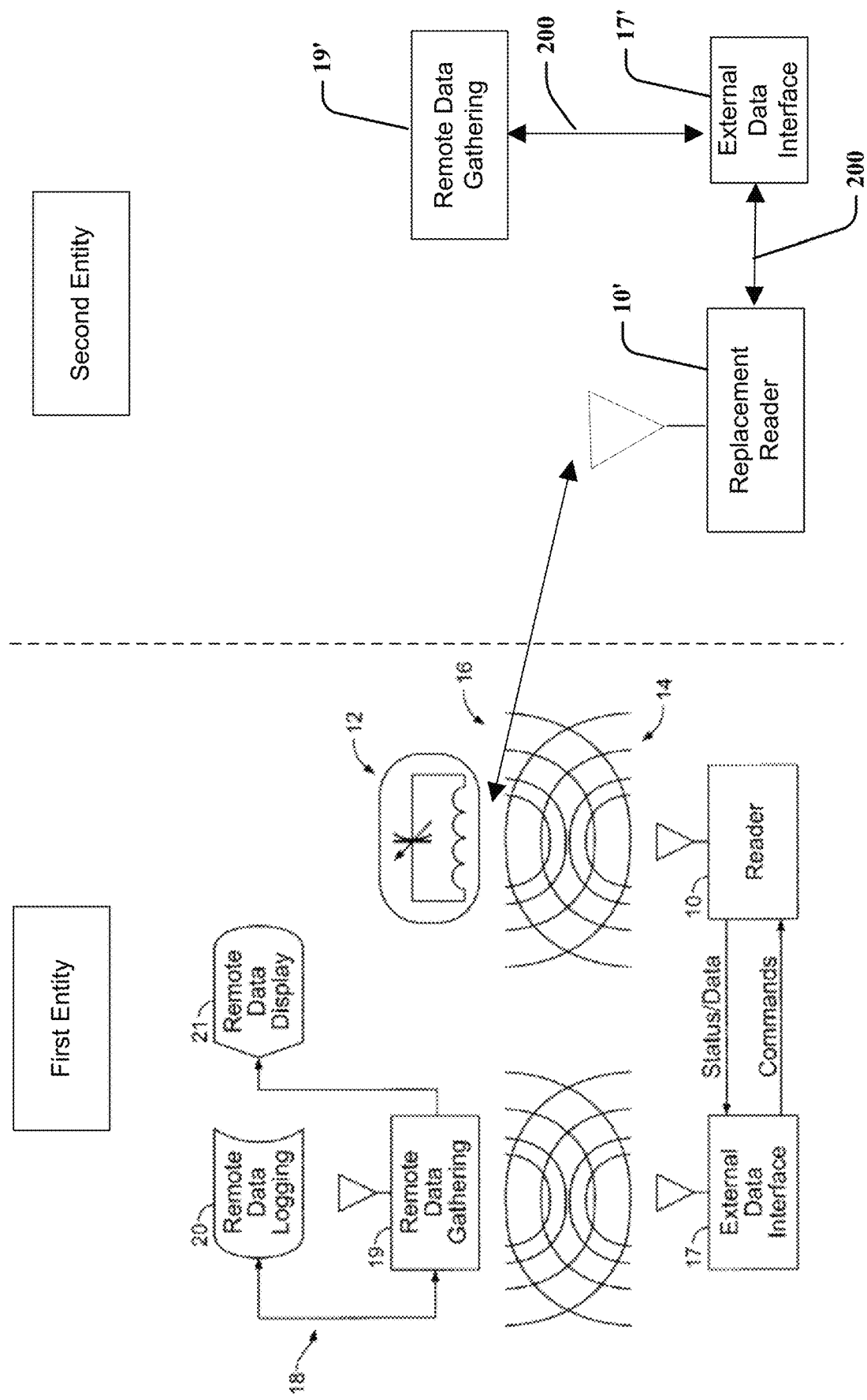
FIG. 7 is a schematic illustration of the replacement reader system, method, and assembly in accordance with the present disclosure.

FIG. 7 illustrates a schematic example of such a replacement reader device 10' and associated system between the first entity and the second entity. Typically, a first entity will provide both the wireless implant 12 and an external reader device 10 at the time of implantation. But during or after implantation, a second entity, that may not be associated with the first entity, may provide another external reader device 10' to be used in place of the first entity's existing reader device 10 to communicate with the implant device 12 with a communication protocol 200 proprietary to the second entity. The "replacement" external reader device 10' may be particularly useful with implant devices 12 that communicate wirelessly with a reader 10 where said implant devices 12 are intended to be located within the human body on a permanent or indefinite duration of time. With such a system, the prescribing physician has the option to implant a patient with a device 12 provided by a first entity 'A', and use a reader ('external device') 10 that is provided by 'A', or an alternative or replacement reader 10' provided by a second entity 'B'. Further, the physician may make the decision to use reader 10 or replacement reader 10' at the time of initial implantation, or she/he may decide to switch an implanted patient from reader 10 to replacement reader 10', or back again, at any time after implantation and discharge from the hospital, even many years later.

Figure 8:
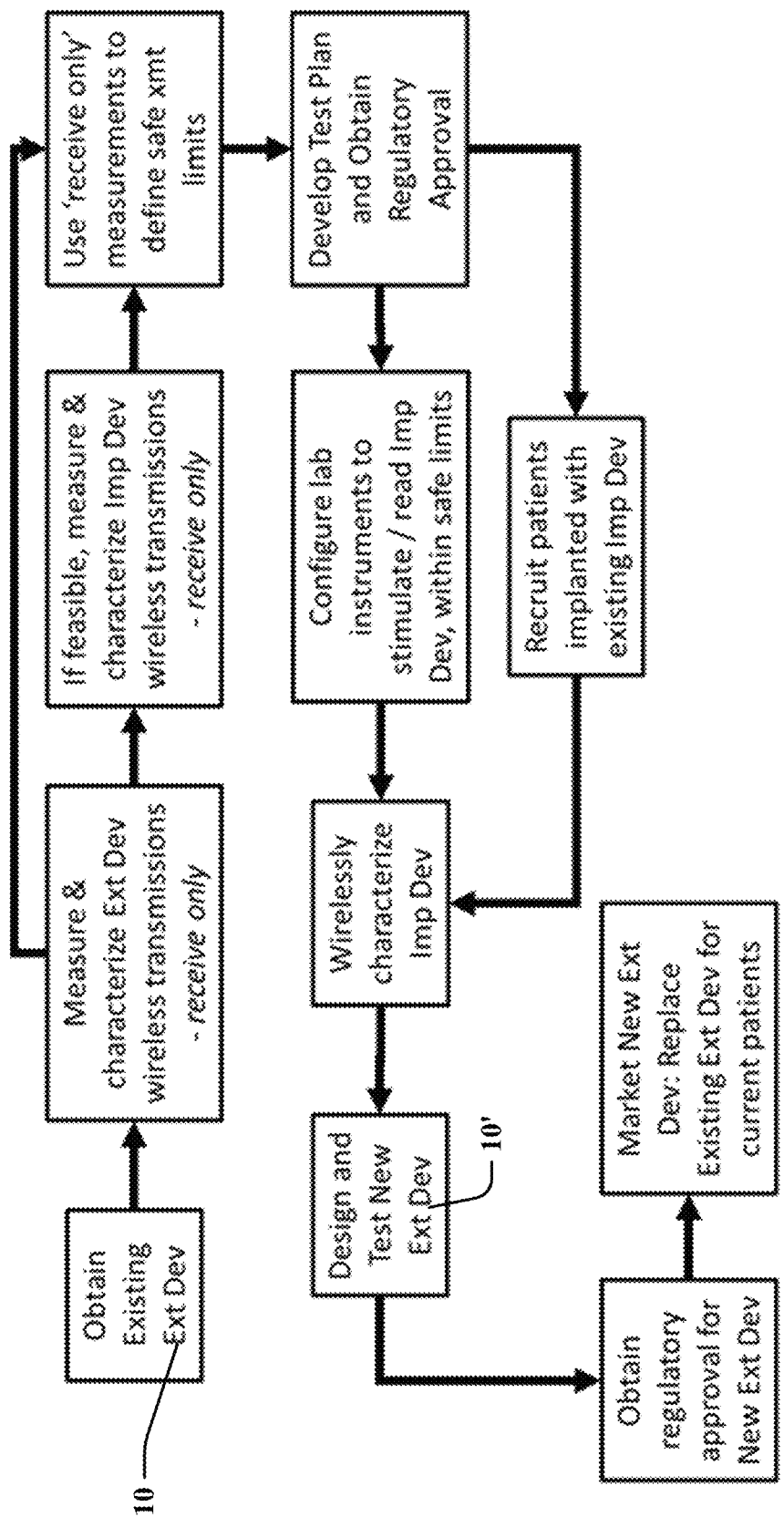
FIG. 8 illustrates a flow diagram describing an embodiment of a method of communicating with implant devices in accordance with the present disclosure.

FIG. 8 illustrates a process for creating a communication system for a wireless implant device 12 that has already been surgically implanted in a patient and is intended to remain permanently implanted. The flowchart of FIG. 8 illustrates the steps for designing, developing, verifying, and validating a replacement external reader device 10' for an implanted device 12 that ensures compatibility with associated proprietary infrastructure such as power and data communications, without having access to a non-implanted implantable device 12 that could be tested on the benchtop. The figure describes a methodology for carrying out such a development using implant devices 12 that are already implanted in the bodies of living patients. The design and development methodology allows full compatibility testing of new replacement reader 10 prototypes with the existing implants 12, while ensuring the safety of the implanted patients.

Figure 9:
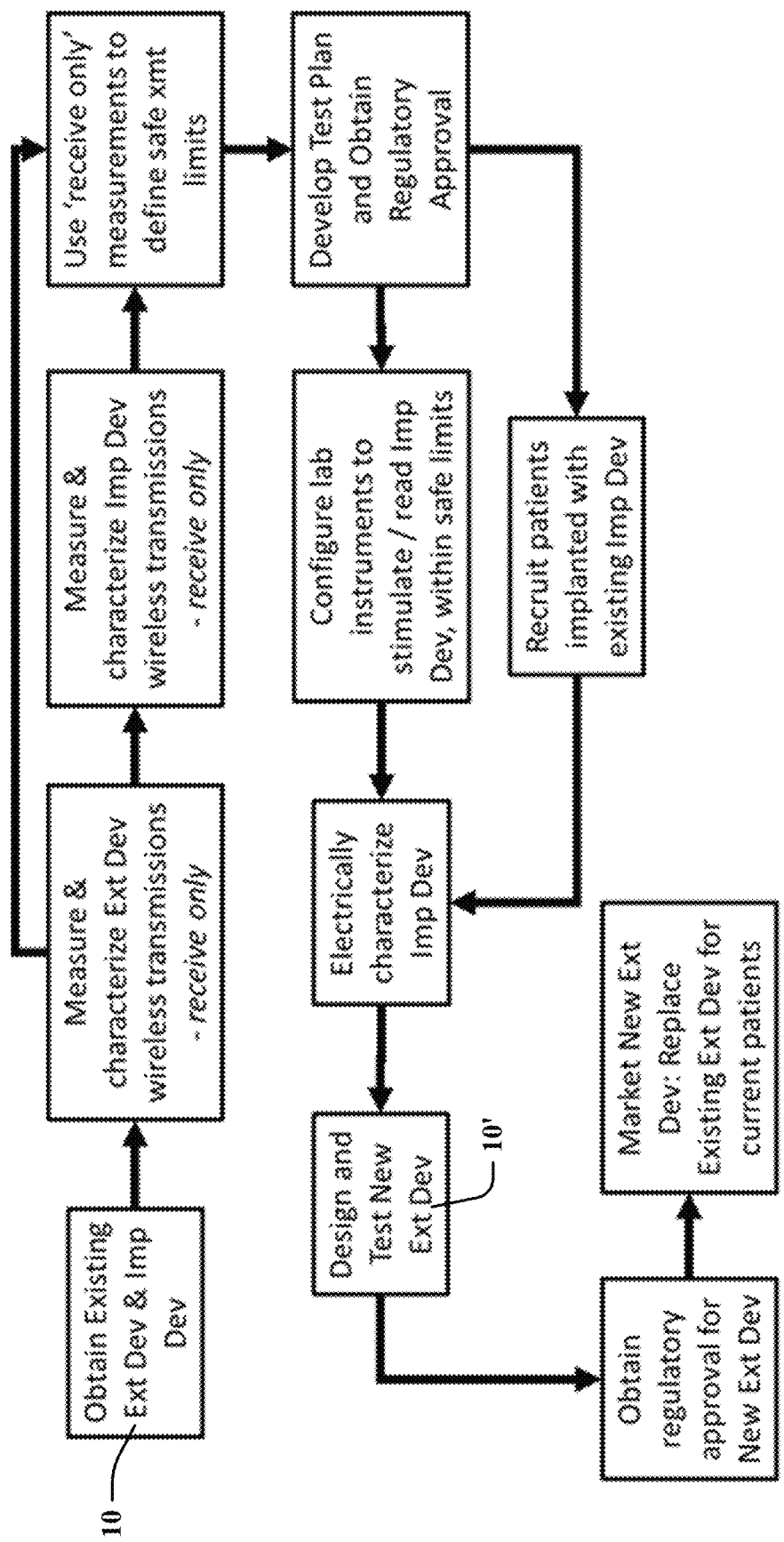
FIG. 9 illustrates a flow diagram describing an embodiment of a method of communicating with implant devices in accordance with the present disclosure.

Similarly, FIG. 9 illustrates a process for creating a communication system for a wireless implant device 12 located within a patient. However, in this process the creation of replacement external devices 12 for the implanted device 12 has the benefit of an implantable device 12 that is available for benchtop testing and has not yet been implanted into a patient.

As an initial matter, the disclosed methods prioritize and ensure the safety of the patients and any other human test subjects throughout the process. They include the step of confirming the type of implant device 12 positioned within the patient as well as associated external reader device 10 (and its related background infrastructure and proprietary communication protocols, e.g., reference numbers 17-21). The source for identifying these items may usually be the medical records of the patient with the currently installed implant device 12. Patients with the 'first entity' device 12 implanted may be recruited as test subjects in the manner commonly known to those in the medical device industry, and may be offered consideration for their participation in the research. Physician oversight, as well as hospital ethics panels and/or institutional review board approval are typically required prior to such research activities.

FIGS. 8 and 9 include the term, "Ext Dev" which means the external reader devices 10 or replacement reader devices 10' that interface functionally with the implanted device 12 to obtain information such as sensor data ("raw data") from a response signal 16, or to initiate action in the case of an implanted device 12 that includes an implanted actuator or sensor. The external device may include the reader 10, docking station 110, external data interface 17, and data gathering system 18. The new or replacement external device may include the replacement reader 10', a docking station 110', external data interface 17', and data gathering system 18' associated with the replacement reader 10'. Implant device 12 or "Imp Dev" may be the implant. It may be an active sensor that includes an internal battery or may be a passive sensor that is externally powered. It may also be a device that includes an actuator to perform a function within the body such as release drugs or perform a movement. It may communicate with the external reader devices electronically, optically, ultrasonically, mechanically, or by other means.

The methods described herein contemplate that an implant device 12, associated external devices 10/110 and 10'/110', and related communication infrastructure and protocols may include components or features that are associated and proprietary to a first entity A or may be associated and proprietary to a second entity B. It is contemplated that the development of an external reader device 10' by the second entity may be performed by obtaining the first entity's existing external devices 10, 110, such as from an existing patient having an implant device 12 associated with the first entity A infrastructure. These patients may have possession of the external devices 10/110 at home, as well as the implant device 12 inside of them. This may be done in collaboration with a physician who manages such patients, to ensure patient safety, and may also be part of a clinical study approved by relevant ethics panels or review boards. Patients and physicians may be compensated as is common in such studies. Also, the first entity external device 10 may be tested for only limited time intervals such that the development process would not interrupt the patient's required readings using the first entity system.

If an actual implant device 12 associated with the infrastructure and proprietary to first entity can be obtained, then bench or animal testing may be performed using that sample implant before human testing may be performed. However, it is also contemplated that first entity implant devices 10 are generally not available outside of the first entity and its authorized medical customers, and especially not to the second entity. Possible methods for the second entity to obtain implant 12 samples for benchtop use may include: (i) purchase through $3^{rd}$ parties who have access to implants 12; (ii) business negotiation with the first entity, resulting in an exchange, license or purchase arrangement; (iii) establishing an agreement with a patient already implanted with the implant 12, wherein the patient gives permission to the second entity to explant her/his sensor 12 after her/his death, said permission may be given in exchange for consideration to the patient before her/his death, or to the patient's family or estate afterwards. External equipment and devices 10/110 belonging to a patient may also be obtained in the same way.

The received external devices 10/110 may then be measured. In this step, external devices 10, 110, 17, 18, as well as implantable device 12 associated with the first entity A may be operated according to their instructions for use. This operation may be performed in the presence of laboratory equipment designed to sense, capture, and record wireless transmissions or other output signals. For example, if the implant device 12 is a passive LC resonant tank that is powered by inductive coupling from the external device 10, an RF spectrum analyzer connected to a loop antenna may be used to procure or sample a reading from the external device 10 by inductively coupling to a power transmitting antenna of the external device 10. This would allow measurement of the frequency content and duration of the transmitted output signal. An RF power meter may be used to connect to a lab antenna of known characteristics, and measure the output power amplitude of the external device 10. It may be advantageous initially to fully characterize the energizing power output by the external device 10, in order to define safe limits of power that can be applied to the sensor 12. Knowing these safe limits, the developer can ensure that any prototypes of the replacement reader 10' does not damage the implant device 12 in any way. Notably, in the FIG. 8 scenario, where the implant device 12 is implanted in a patient, safety precautions are taken to ensure such steps do not harm the patient.

The measurement of the output of implant device 12 associated with the first entity may additionally be measured if feasible. In this embodiment, measuring and characterizing the reflected signal from the implant device 12, using only power from the external device 10 or other lab equipment, may not be straightforward or even possible using conventional lab instruments. In the embodiment depicted in FIG. 9, samples of an implant 12 are available that are not already implanted in a patient; in such an embodiment bench characterization of the implant 12 and its sensor by standard lab instruments is straightforward. In the FIG. 8 embodiment, however, the implant 12 along with its associated sensor are already implanted in a living patient, and standard lab instruments may not have the ability to energize and read the sensor's signal or ringback signal or wireless signal provided by the sensor of the implant 12. If lab instruments could not be brought to bear, measurement of the implanted sensor would need to be accomplished by custom equipment. In either case, it would be necessary to limit the equipment's energizing signals to the known safe levels originally defined by measuring output from the reader 10 of the first entity.

In another embodiment, the communication between external device 10 and implant device 12 associated with first entity may be performed using a digital based protocol. Here, the implant device 12 may include its own power source such as a battery. In this case, an RF power meter may be implemented to measure and determine power output by the associated external device 10. A wireless listening device may be placed in communication with a packet analyzer or packet sniffer or similar device to record the output signals and associated bit patterns of the external device 10 and implant device 12. Packet analyzers may be a computer program or hardware item that can intercept, capture, and log signal traffic that passes through the air over a wireless digital network. The packet analyzer may decode raw data for illustrating values of various fields within the signal. This process may be replicated several times until the digital signal may be accurately characterized. The output signals of both the external device 10 and the implant device 12 may be sampled and characterized to determine a range of signal values, codes, and bit patterns to assist with safely creating a replacement external device or reader device 10' configured to communicate with the existing implant 12 and associated sensor.

In some embodiments, the implant device 12 may output data without a trigger signal from the external device 10, for example at a certain time of day or in response to a physiological event that it detects. In these cases, it may be feasible to also sample or measure the signal transmitted from the implant device 12 during these predetermined events.

In all embodiments, the measure and characterization step may be performed with lab instruments used to characterize transmitted signals from both the external device 10 and the implant device 12 while in receive only mode. This may allow for un-interruption of signal gathering and may prevent noise as well as unintended coupling of energy from the lab instruments into either external device or implant device. This may assist with preserving the respective devices as range, amplitude, or frequency of energy signals that could damage the respective devices may be unknown at this time.

The safe 'receive only' testing of external device 10, 110 and implant device 12 will indicate safe limits that the new replacement external reader devices 10'/110' are configured to comply with the existing implant device 12 and its associated communication protocols. The measured and characterized wireless transmissions or output signals from the external device 10 and implant device 12 may be used to define safe transmission limits for the replacement reader 10' that will not damage the implant device 12 within the patient. Here, it may be inferred that a power level of the normal transmission signals output by the external device 12 associated with first entity are performed at a safe level and cannot damage the implant device. In this step, the measurements and characterized wireless transmission made on the external device 12 may define a safe limit that can be used in worst case conditions (i.e., shortest distance between implant device and external device). A safety margin may be added to the identified transmission limit. Additionally, further parameters related to the transmit signals may be defined, such as frequency content, duration, burst pattern, bit rate, phase characteristics, polarity (for optical signals), or various other parameters that could potentially damage the implant device by exceeding a threshold limit. Circuit or RF modeling may assist the determination of safe limits given additional parameters such as link distance, Q factor of implant device, Q factor of an antenna of the external device antenna, and intermediate tissue electrical characteristics.

After measuring and characterizing the transmit characteristics of the external devices 10, 110 and defining safe limits to prevent damage to the implant device 12, further steps may be performed to characterize, verify and validate the interaction between the implant device 12 inside of the human patient and the replacement reader device 10'. In nearly all jurisdictions, clinical testing such as this requires approval from a regulatory body; for example, from an authorized Institutional Review Board (IRB) and/or Ethics Panel at a hospital or clinic. These bodies typically require a detailed test protocol, as well as risk analysis based on bench test results showing the testing will not expose patients to hazards. They also typically require informed patient consent to be documented, among other things. Once the characterization of the original external device 10 is complete and documented verification of safety is established, a clinical test protocol is developed and regulatory approval for human testing may be pursued.

During testing, lab instruments may be configured to stimulate, read, or sample data from the implant device 12 to safely determine the characteristics of the implant device within the patient. In one embodiment, the implant device 12 may be a wireless, battery-less LC resonant tank device that changes its resonant frequency in response to changes in pressure. Here, a lab grade impedance analyzer, such as the Keysight E4990A connected to a custom test antenna, may be used to wirelessly sweep a low-power transmit signal across a pre-defined band of frequencies. This test may be able to provide an output signal to characterize about a center frequency of the sensor. Additionally, a reader device such as the one described in U.S. Pat. Nos. 8,154,389, 8,432,265, 8,493,187, 8,570,186, 9,305,456, 9,489,831, 9,721,463, and 9,894,425, all of which are incorporated by reference to perform this step. In both cases, the instrument used to stimulate and receive a ring signal from the implant device may need to be adjusted or modified to ensure safe power limits are not exceeded at the implant device 12, and that the instrument acting as the new external device (or reader) 10' is configured to transmit and receive frequencies in the range of operation of the implant device 12. In the embodiment using a lab instrument, this may be done by adjusting settings. In the embodiment using a dedicated reader device, the reader circuit design may require modification.

In another embodiment, the implant device 12 may be a digital device, possibly with its own battery or energy harvesting system. Here the lab instrument may be configured to mimic an external device's proprietary protocol associated with the first entity. The lab instrumentation may be a pattern generator, sequencer, FPGA, processor-based or other digital device connected to a power amplifier and an antenna. The lab instrumentation may identify or produce a bit pattern, decoded or identified in a previous step, that causes the implant device 12 to generate output data in accordance with its proper function within the patient. The lab instrumentation may be configured, by adjustment, calibration, or design, to ensure that transmit signals remain within the predefined safe limits.

Patients having received implant devices 12 associated with first entity may be recruited once regulatory approval is in place. Patients who have already been implanted with the existing device may participate on a voluntary or paid basis, as permitted by local regulations. Typically, implanted patients will come to the laboratory where the new or replacement external device 10' is being developed.

Following the approved protocol and adhering to the defined safe limits, lab instruments may be configured to mimic the original reader devices 10, by characterizing or communicating with the implanted device 12 inside the patient in a wireless manner. Here electrical, optical, ultrasonic or other relevant means may be used to wirelessly characterize the implant device. Participation in these measurements should not cause risk or discomfort to the patient, and should not interfere with his/her normal regimen for using the existing external device from the first entity. Once the measurement, signal characterizations and wireless characterizations of the implant device 12 have been completed, the design, development, and testing of new or replacement external device 10' may be performed. This may include activities associated with development of any new medical device of this nature, according to required design control standards such as the FDA's *Design Control Guidance for Medical Device Manufacturers*. Development may include various levels of bread-boarding and prototyping, building implant device emulators that mimic the electrical characteristics of the actual implant device for benchtop testing, and finally testing with the implanted live subjects previously recruited. Use of emulators may reduce the amount of live subject testing needed during development. Development, as well as final verification and validation of the new external device may also include comparison testing between the first entity's existing external device 10 and second entity's newly developed external device 10'.

The new external device may then proceed to regulatory approval. Depending on the jurisdiction and the final product, this will likely involve quality control, product listing, pre-clinical, and/or clinical validation. In general, this means a 510k listing or a PMA trial in the United States, or CE Mark approval in Europe and elsewhere. A clinical trial for such a new replacement reader may involve a study in which a statistically significant number of patients already implanted with the device of the first entity use the already approved external devices 10/110 of first entity to communicate with their implanted device, and then repeat the communication using the external devices of the second entity. The trial may attempt to demonstrate functional equivalence between the communication results of the associated external devices.

With regulatory approval secured, the newly created external replacement devices from the second entity may be used in place of the external devices 10/110 associated with the system and implant device of first entity. The new or replacement external devices may replace the original external devices and be compatible with the backend infrastructure associated with second entity and its proprietary communication protocol and be used by patients already implanted with the existing implant device associated with the first entity.

Once the second entity's external device is approved for sale, a clinician may initiate this method by prescribing a patient already implanted with an implant 12 and using a reader 10 with a new or replacement reader 10'. This step may include a calibration process at the time of replacement. To calibrate, at least one reading is made using the existing external device 10, and the results used to calibrate the new external device 10', for example by applying an offset, a sensitivity adjustment, or other mathematical adjustment. In different embodiments, the measured calibration coefficients could be applied either at the local external device level, or further upstream in the data chain, such as in a cloud-based data processing engine.

In one embodiment, the implant 12 may be a sensor device that must be calibrated against a known reference in order to achieve sufficient accuracy. This is usually due to manufacturing variances in individual implants and sensors that cause error, and so every sensor may have a unique characteristic. After implant, the reading taken from the implant 12 may be compared to a reading taken from a trusted reference device and the difference recorded; the external device 10, or an upstream storage devices (i.e., 17 or 19) then stores calibration coefficients based on that difference and uses it to correct all future readings from that sensor/reader combination mathematically. When a replacement reader device is being activated or coupled to the system of the first entity, the replacement reader 10' may be recalibrated to properly communicate with the new system. That is, the new implant 12 and reader 10' combination include unique calibration coefficients that are identified and stored for application with future readings.

Figure 10:
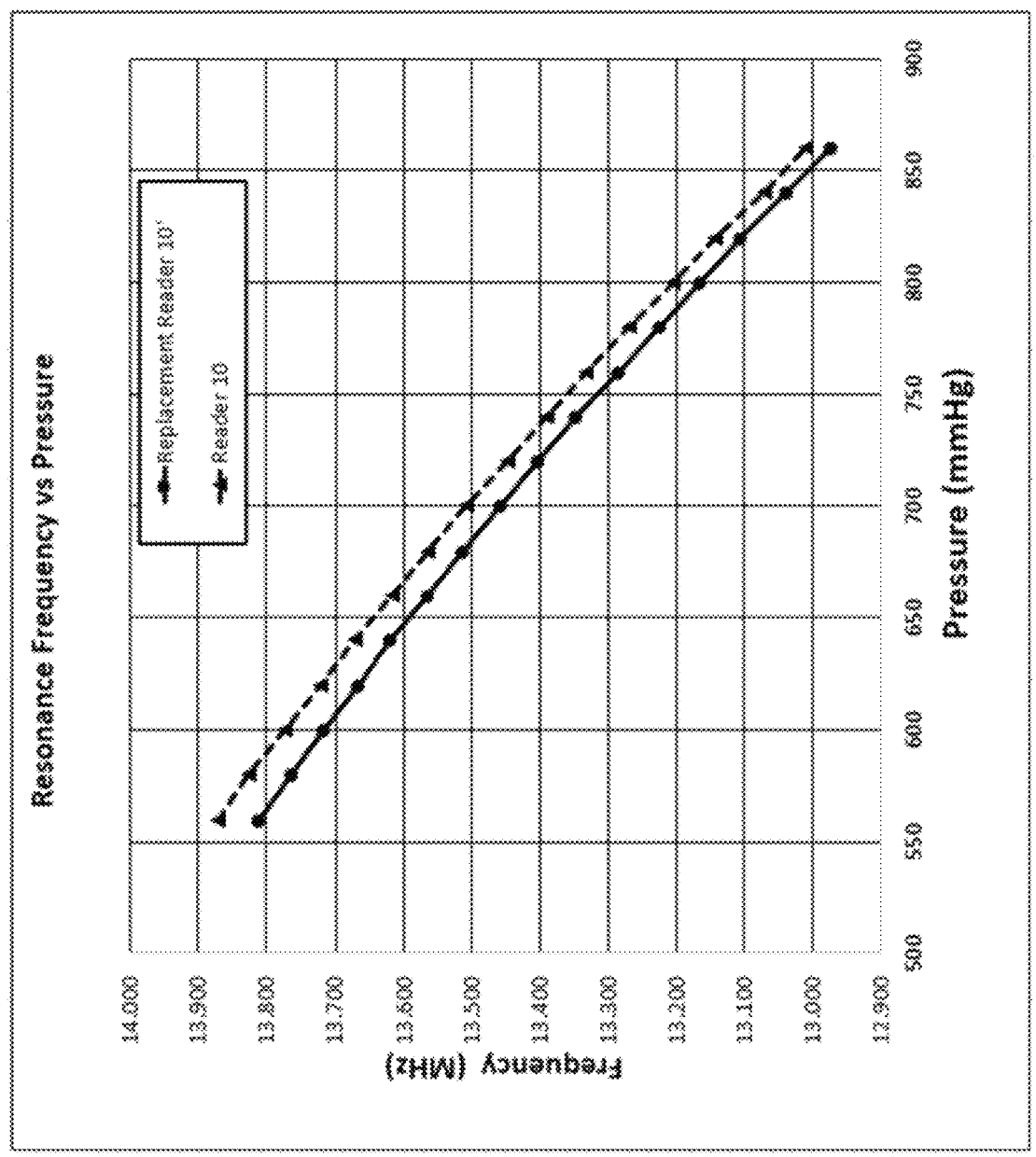
FIG. 10 is a graph that illustrates a typical sensitivity curve for an exemplary LC resonant tank pressure sensor as read by an original reader device and a replacement reader device, to demonstrate the concept of using a reference to calibrate the other after taking simultaneous or near-simultaneous readings.

As an example, a pulmonary artery (PA) pressure sensor configured as an LC resonant tank may transduce pressure to a resonant frequency according to a characteristic exemplified in FIG. 10. For each pressure level on the x-axis, Sensor from the implant 12 resonates at a unique corresponding frequency on the y-axis. All the points across the pressure range of the implant 12 form a frequency-to-pressure characteristic curve shown as a dashed curve in FIG. 10. The system associated with the first entity may characterize this curve at its factory and may fit it to a polynomial or other type of equation or lookup table. This curve or lookup table may be used to calculate coefficients that can be applied to raw frequency data received from a unique implant in order to accurately convert the raw frequency values to usable output data such as measured pressure. Those coefficients (or lookup table values) may be used to convert raw frequency data to output pressure data for future readings.

Each implant 12 may include a unique frequency-to-pressure characteristic curve is known to the first entity but may be unknown to a second entity at the time of a replacement reader 10' is being implemented or otherwise coupled for continuous future use with the existing implant 12. Therefore, technical or clinical staff, with the cooperation of the patient, re-calibrate the new combination of the implant 12 and the replacement reader 10'. This may be accomplished by taking simultaneous or near-simultaneous readings of the implant 12 with both the existing reader 10 and the replacement reader 10', with the readings taken by the existing reader 10 serving as the reference standard. Here near-simultaneous refers to a time interval over which the measured data is unlikely to change significantly. If the measurement is PA pressure, for example, near-simultaneous may be one minute or less when the patient is in a stable state. A reading from the existing reader 10 and a reading from the replacement reader 10' of the same implant 12 in a patient may be taken while the patient is maintained at rest and in a same general position. These readings may be taken at different PA pressures of the patient until a sufficient number of data points exist to curve fit both the existing reader 10 and the replacement reader 10' characteristic curves for the a pressure range, using curve fitting techniques. With sufficient data points obtained, calibration data can be extrapolated from both the solid and the dashed curves shown in FIG. 10. The original curve from data points measured by the original reader 10 is considered to be the accurate reference standard. The difference between the original reader 10 curve and the replacement reader 10' curve coefficients is noted, and replacement reader coefficients may be derived such that applying the replacement reader coefficients to future raw frequency data from readings taken by the replacement reader 10' may be applied to yield accurate pressures that are comparable to readings taken by the original reader 10 and system of the first entity. The new coefficients are stored in the associated system related to the replacement reader 10' and applied to each future reading by an appropriate algorithm, either in the reader 10' or an upstream device such as the external data interface 17', or the remote data gathering 19' modules.

In an embodiment, accurate coefficients may be procured for use in calibration of the replacement reader 10' and may be procured when measuring readings near the extrema of the system's pressure range. This may be performed by altering the patient's actual PA pressure when readings are taken by the reader 10 and replacement reader 10'. Methods for safely altering the patient's PA pressure may include taking readings of a patient when placed in the following states: relaxation versus exertion (e.g. aerobic exercise); Valsalva maneuver; seated vs standing vs supine posture; elevated legs; supine or prone position with body tilt towards head versus towards feet; medications, or other forms of applying stress to the patient to modify PA pressure.

The previous example from FIG. 10 is specific to LC resonant tank pressure sensors in the pulmonary artery "PA". It exemplifies the general concept of calibrating a replacement reader 10' and its interaction with an implant 12 associated with proprietary communication protocols of a first entity while using the original reader device 10 as a measurement reference. The objective of the calibration steps is to identify mathematical or lookup-table data to process the outputs taken or measured from the original reader 10 such that it will consistently match or be comparable outputs taken or measured from the replacement reader 10' when sensing the same measured parameter.

Alternatively, a clinician may choose to implant a patient with the implant device, but use the replacement reader devices from the start. In this scenario, the system may be calibrated in the manner using a simultaneous known reference measurement such as a right heart catheter to compare against the readings taken by the replacement reader 10', and generating calibration coefficients to apply to future readings.

FIG. 9 illustrates a similar concept but with the advantage of having a bench implant that is not located within a patient wherein this bench implant is available from the beginning of the process. A great deal of bench development can be performed using only the non-implanted bench devices.

Notably, this method and system may be adopted for existing implant devices that are configured to provide various ongoing chronic care management services where a permanent (or long-term) implant communicates power or data with an external device in an out-patient setting or in-patient setting.

The embodiments of the disclosure have been described above and, obviously, modifications and alternations will occur to others upon reading and understanding this specification. The claims as follows are intended to include all modifications and alterations insofar as they are within the scope of the claims or the equivalent thereof.

The invention claimed is:

1. A method for providing a device configured to wirelessly communicate energy, data, or commands with an implant device located within a human body, said method comprising the steps of:
   obtaining a first external device configured to wirelessly transfer energy, data, or commands to or from said implant device, wherein said first external device communicates with said implant device through a first proprietary protocol of a first entity;
   generating a plurality of first signals from said first external device;
   characterizing said first signals to determine input limits for said implant device, said input limits being related to a range of signal outputs that have a reduced risk of damage to said implant device or harm to said human;
   creating a second external device using said range of signal outputs from said first external device to communicate energy, data, or command signals between said second external device and said implant device wherein said second external device is associated with a second entity wherein said second external device is configured to wirelessly communicate with said implant device and wherein said second external device is configured to replace said first external device.

2. The method of claim 1 further comprising the step of using said first external device to calibrate said second external device for use with said implant device.

3. The method of claim 1 wherein said implant device includes at least one of a sensor and an actuator located in the cardiovascular system of a patient.

4. The method of claim 3 wherein said implant device is located in the pulmonary artery of said patient.

5. The method of claim 3 wherein said implant device is configured to sense pressure.

6. The method of claim 1 wherein said implant device comprises an LC resonant tank.

7. The method of claim 1 wherein said implant device is surgically implanted within said patient via a minimally invasive surgical procedure.

8. The method of claim 1 wherein said implant device includes a glass housing having nitinol anchors.

9. The method of claim 1 wherein said implant device is configured to wirelessly receive or transmit digital signals or analog signals.

10. The method of claim 1 wherein said implant device is configured to provide a ring back signal having a frequency that corresponds to the measured value.

11. The method of claim 1 wherein said implant device is selected from one of: an electronic device, an optical device, a mechanical device, an ultrasonic device, a drug eluting device, a neurostimulation device, a cardiac pacing device, an electrocardiogram device, a vessel diameter measurement device, and a fibrillation monitor.

12. The method of claim 1, wherein said implant device is not implanted in a human.

13. A method for providing a clinician with physiological data obtained from a plurality of patients in remote locations, said method comprising:
provinding patients with a first implant device that is operable to communicate physiological data wirelessly to a first external device, each of the first implant devices and the first external devices communicate via a first protocol;
identifying patients having a second implant device that wirelessly communicates physiological data to a second external device via a second protocol, where said second implant device is not operable to wirelessly communicate with said first external device;
creating a third external device that is operable to wirelessly communicate with said second implant device;
wherein:
(i) said first and second implant devices include a sensor and said first, second, and third external devices are configured to acquire readings from a sensor;
(ii) further comprising the step of calibrating the third external device by taking at least one near-simultaneous reading of said sensor of the second implant device with said second and said third external devices;
(iii) said second external device's reading is configured to be a reference reading used to calculate calibration coefficients; and applying said calibration coefficients to said third external device when said third external device takes readings of said second implant device.

14. The method of claim 13 wherein said first external device and said third external device are configured to communicate via the first protocol.

15. The method of claim 13 wherein said first protocol and second protocol includes hardware and software used to aggregate, store, process, transmit, relay, format, packet, manage, analyze, and display said physiological data.

16. The method of claim 13 further comprising the step of using said third external devices in place of said second external devices for patients that have said second implant device.

17. The method of claim 13 further comprising the step of calibrating said third external device by using said second external device to take reference measurements of said second implant device; taking initial measurements from said second implant device by the third external device; comparing said reference measurements of said second implant device with said initial measurements taken of said second implant device by said third external device; and calibrating the third external device.

18. The method of claim 13 wherein said implant device is at least one of a sensor and an actuator that is located in the cardiovascular system of a patient.

19. The method of claim 18 wherein said implant device is configured to sense pressure.

20. The method of claim 13 wherein said implant device is configured to wirelessly receive or transmit digital or analog signals.

21. The method of claim 13 wherein said implant device is configured to provide a ring back signal having a frequency that corresponds to the measured value.

22. The method of claim 13 wherein said implant device is selected from one of: an electronic device, an optical device, a mechanical device, an ultrasonic device, a drug eluting device, a neurostimulation device, a cardiac pacing device, an electrocardiogram device, a vessel diameter measurement device, and a fibrillation monitor.

23. The method of claim 13 wherein a plurality of near-simultaneous calibration readings are taken at different points within the sensor's range.

24. The method of claim 23 wherein said sensor is a pulmonary artery pressure sensor and said different points within the sensor's range are created by one of the following methods: relaxation versus exertion; Valsalva maneuver; seated vs standing vs supine posture; elevated versus lowered limbs; supine or prone position with body tilt towards head versus towards feet; medications.

* * * * *